US012780974B2

(12) United States Patent
Guo et al.

(10) Patent No.: US 12,780,974 B2

(45) Date of Patent: Nov. 3, 2026

(54) BIOMAGNETIC MICROSPHERE AND PREPARATION METHOD AND USE METHOD THEREFOR

(71) Applicant: KANGMA-HEALTHCODE (SHANGHAI) BIOTECH CO., LTD., Shanghai (CN)

(72) Inventors: Min Guo, Shanghai (CN); Liang Wu, Shanghai (CN); Liqiong Xu, Shanghai (CN); Zheng Zhang, Shanghai (CN); Jie Su, Shanghai (CN); Xue Yu, Shanghai (CN)

(73) Assignee: KANGMA-HEALTHCODE (SHANGHAI) BIOTECH CO., LTD., Shanghai (CN)

( * ) Notice: Subject to any disclaimer, the term of this patent is extended or adjusted under 35 U.S.C. 154(b) by 755 days.

(21) Appl. No.: 17/621,432

(22) PCT Filed: Jun. 19, 2020

(86) PCT No.: PCT/CN2020/097155

§ 371 (c)(1),
(2) Date: Dec. 21, 2021

(87) PCT Pub. No.: WO2020/253834

PCT Pub. Date: Dec. 24, 2020

(65) Prior Publication Data

US 2022/0372196 A1 Nov. 24, 2022

(30) Foreign Application Priority Data

Jun. 21, 2019 (CN) ......................... 201910540132.6

(51) Int. Cl.
*C08F 292/00* (2006.01)
*C07K 1/22* (2006.01)

(52) U.S. Cl.
CPC .............. *C08F 292/00* (2013.01); *C07K 1/22* (2013.01)

(58) Field of Classification Search
CPC ................................ C08F 292/00; C07K 1/22
See application file for complete search history.

(56) References Cited

U.S. PATENT DOCUMENTS

| | | | | |
|---|---|---|---|---|
| 8,664,350 | B2 * | 3/2014 | Thetford | C09C 3/10 524/13 |
| 9,580,560 | B2 * | 2/2017 | Mattoussi | C09D 123/36 |
| 10,669,475 | B2 * | 6/2020 | Naasani | C09K 11/623 |
| 2013/0028857 | A1 * | 1/2013 | Gao | A61P 31/00 977/773 |
| 2013/0149772 | A1 | 6/2013 | Lee | |
| 2014/0206822 | A1 * | 7/2014 | Joo | A61K 47/6929 556/9 |
| 2016/0069871 | A1 * | 3/2016 | Ueya | C08F 292/00 435/6.1 |
| 2017/0306072 | A1 * | 10/2017 | Fonnum | C08F 293/005 |
| 2019/0359884 | A1 * | 11/2019 | Naasani | H10H 20/8512 |
| 2021/0065943 | A1 * | 3/2021 | Zhang | C08K 3/22 |

FOREIGN PATENT DOCUMENTS

| | | |
|---|---|---|
| CN | 103406100 | 11/2013 |
| CN | 103406100 A | 11/2013 |
| CN | 104402003 A | 3/2015 |
| CN | 104402003 | 5/2015 |
| WO | 2013149772 | 10/2013 |

* cited by examiner

*Primary Examiner* — Jane L Stanley
(74) *Attorney, Agent, or Firm* — Clement Cheng

(57) ABSTRACT

The present invention relates to a biomagnetic microsphere and a preparation method and a method for protein isolation and purification therefor. The outer surface of a magnetic microsphere body of the biomagnetic microsphere has at least one liner polymer with a branched chain; one end of the linear polymer with a branched chain is covalently coupled to the outer surface of the magnetic microsphere body, and other parts are free on the outer surface of the magnetic microsphere body; a backbone of the linear polymer is a polyolefin backbone, and no cross-linking agent is required in the backbone forming process of the linear polymer. The prepared biomagnetic microsphere can implement efficient elution of target proteins and effectively reduce the retention time and retention ratio of the target proteins, and it is easy to operate and widely used.

11 Claims, 4 Drawing Sheets

BIOMAGNETIC MICROSPHERE AND PREPARATION METHOD AND USE METHOD THEREFOR

The present application claims priority to Chinese Patent Application No. CN 2019105401326, filed on Jun. 21, 2019, the entire content of which is incorporated herein by reference.

BACKGROUND OF THE INVENTION

1. Technical Field

The present invention relates to the field of biotechnology, and more particularly, to a biomagnetic microsphere and a preparation method therefor and a method for protein isolation and purification using the biomagnetic microsphere.

2. Description of the Related Art

Protein isolation and purification is widely used in a plurality of fields including manufacture of a biopharmaceutic, detection and diagnosis of a biological protein molecule, analysis of a protein structure and more. In the prior art, a plurality of commonly used techniques for protein isolation and purification comprise a nickel column, a Protein A column, a biotin column, and more. In the technique of the nickel column, a histidine-tagged protein can be isolated from a mixed system by a nickel ion immobilized on a carrier. At this stage, a commonly used carrier is agarose gel. A three-dimensional porous structure of a gel material facilitates an increment of a specific surface area of the material, so that sites for immobilizing the nickel ions are increased and a capacity to binding to a target protein is enhanced.

Thanks to the three-dimensional porous structure of the material, the number of a plurality of target proteins binding sites can be greatly increased, however, the porous structure inside the material can also increase a retention time of the proteins when the proteins are eluted, and a plurality of discontinuous space or dead corners inside the material will prevent the proteins from being eluted from an interior of the material, thereby increasing a retention ratio. If the target proteins binding sites are immobilized only at an outer surface of the material, a target protein can be prevented from entering the interior of the material, then the retention time and the retention ratio of the target proteins can be greatly reduced during a process of elution. However, if only the outer surface of the material is used, the specific surface area of the material will be greatly reduced, and the number of the target proteins binding sites will be greatly reduced.

A polymer is a macromolecular compound obtained by polymerization of a plurality of monomer molecules. After being polymerized, the monomer molecules with active sites can enable an obtained polymer to have a large number of active sites, thereby increasing the number of the active sites. By the active sites, a plurality of corresponding binding sites can be further coupled. There are many types of polymers, including polymers in which molecular chains are cross-linked to form a network structure, polymers with single linear molecular chains, polymers with many branched chains, and more. Different types of the polymers have different wide applications in different fields respectively.

SUMMARY OF THE INVENTION

The present invention provides a biomagnetic microsphere and a preparation method therefor and a method for protein isolation and purification using the biomagnetic microsphere. The biomagnetic microsphere is a functionalized magnetic microsphere, and the isolation and purification of the target proteins are carried out only by using the outer surface of the magnetic microsphere; the outer surface of the magnetic microsphere is modified with a linear polymer with a branched chain, so that it is possible to achieve a high-efficiency and high-throughput binding of the target proteins, while effectively reducing the retention time and the retention ratio of the target proteins during the process of elution.

According to a first aspect, the present invention provides a biomagnetic microsphere, wherein the biomagnetic microsphere has a magnetic microsphere body, the outer surface of the magnetic microsphere body has at least one liner polymer with a branched chain; one end of the linear polymer with the branched chain is covalently coupled to the outer surface of the magnetic microsphere body, a backbone of the linear polymer is a polyolefin backbone, the branched chain of the linear polymer contains a functional group, and the functional group can bind to a target object.

In one of the preferred embodiments, the linear polymer is obtained by polymerization of one selected from a group comprising acrylic acid, acrylate, acrylic ester, methacrylic acid, methacrylate, methacrylic ester, other acrylic monomers, and a combination thereof; preferably, no cross-linking agent is required in a backbone forming process of the linear polymer.

The branched chain of the linear polymer contains a functional group, and the functional group is able to bind to a target object. Preferably, the branched chain of the linear polymer contains a specific binding site (i.e., the functional group is the specific binding site), and the specific binding site can specifically bind to the target object.

More preferably, the specific binding site is a nickel ion, the nickel ion is able to specifically bind to a label of a His tag.

In one of the preferred embodiments, the functional group of the linear polymer is one selected from a group comprising carboxyl, hydroxyl, amino, sulfhydryl, and a combination thereof.

In one of the preferred embodiments, the linear polymer is directly fixed to the outer surface of the magnetic microsphere body, or indirectly fixed to the outer surface of the magnetic microsphere body through a linking group.

In one of the preferred embodiments, the magnetic microsphere body is a $SiO_2$-coated magnetic particle.

In one of the preferred embodiments, the magnetic particles have a chemical component comprising one selected from a group comprising iron compounds, iron alloys, zinc oxides, manganese oxide mixture, gadolinium oxide mixture, cobalt compounds, nickel compounds, nickel alloys, manganese oxides, manganese alloys, zinc oxides, gadolinium oxides, chromium oxides, and a combination thereof.

In one of the preferred embodiments, the magnetic particles have a chemical component comprising one selected from a group consisting of iron oxides, zinc oxides, manganese oxide mixture, gadolinium oxide mixtures, cobalt oxides, nickel oxides, manganese oxides, zinc oxides, gadolinium oxides, chromium oxides, and a combination thereof.

In one of the preferred embodiments, the magnetic particles have a chemical component comprising one selected from a group consisting of iron oxide, iron, cobalt, $Co^{2+}$, iron nitride, $Mn_3O_4$, GdO, nickel, $Ni^{2+}$, and a combination thereof; wherein, the iron oxide is preferably $Fe_3O_4$, $\gamma$-$Fe_2O_3$, or a combination thereof.

In another one of the preferred embodiments, the magnetic particles have a chemical component comprising one selected from the group consisting of $Fe_3O_4$, $\gamma$-$Fe_2O_3$, iron nitride, $Mn_3O_4$, AlNi(Co), FeCr(Co), FeCrMo, FeAlC, AlNi (Co), FeCrCo, ReCo, ReFe, PtCo, MnAlC, CuNiFe, AlMnAg, MnBi, FeNi(Mo), FeSi, FeAl, FeNi(Mo), FeSiAl, $BaO \cdot 6Fe_2O_3$, $SrO \cdot 6Fe_2O_3$, $PbO \cdot 6Fe_2O_3$, GdO, and a combination thereof; wherein Re is rhenium, which is a rare earth element.

According to a second aspect, the present invention provides a method for preparing the biomagnetic microsphere according to the first aspect of the present invention, comprising a plurality of steps including:

(1) performing a chemical modification to the magnetic microsphere body, by introducing an amino group onto the outer surface of the magnetic microsphere body before forming a magnetic microsphere A;

in one of the preferred embodiments, the chemical modification to the magnetic microsphere body is carried out with a silane coupling agent;

(2) coupling an acrylic acid molecule covalently onto the outer surface of the magnetic microsphere A by using a covalent reaction between carboxyl and the amino group, so as to introduce a carbon-carbon double bond and form a magnetic microsphere B;

(3) in absence of the cross-linking agent, polymerizing the acrylic monomer molecules by a polymerization reaction between the carbon-carbon double bond, having an obtained linear polymer covalently coupled to an outer surface of the magnetic microsphere B, before performing a solid-liquid separation and removing a liquid phase to obtain a magnetic microsphere C;

if the functional group contains the specific binding site, the method further comprises a step of: (4) coupling the specific binding sites at a branched chain of a linear polymer of the magnetic microsphere C;

in one of the preferred embodiments, the acrylic monomer molecule is a sodium acrylate monomer molecule.

The Steps (1) and (2) described above can be combined into a following Step (I): performing a chemical modification to the magnetic microsphere body by adopting a trimethoxysilanized acrylic molecule, and introducing a carbon-carbon double bond onto the outer surface of the magnetic microsphere body, before forming the magnetic microsphere B.

The trimethoxysilanized acrylic molecule can be, for example, $\gamma$-methacryloxy propyl trimethoxyl silane (KH570 acyloxysilane, CAS: 2530-85-0).

In one of the preferred embodiments, the branched chain of the linear polymer of the magnetic microsphere C contains the nickel ion. In the present embodiment, the method further comprises a step of: (4) coupling tricarboxylic amine to the magnetic microsphere C, before complexing $Ni^{2+}$ to three carboxyl groups in a residue of the tricarboxylic amine to obtain a magnetic microsphere D, that is, a target biomagnetic microsphere; wherein the target biomagnetic microsphere can bind to a label of the His tag specifically.

In one of the preferred embodiments, the tricarboxylic amine is N,N-bis(carboxymethyl)-L-lysine, and the amount of the N,N-bis(carboxymethyl)-L-lysine is preferably in a range from 0.5 g/L to 550 g/L.

In one of the preferred embodiments, the amount of the acrylic acid for preparation of the magnetic microsphere A in Step (2) is in a range from 0.002 mol/L to 20 mol/L.

In one of the preferred embodiments, the amount of the sodium acrylate for preparation of the magnetic microsphere B in Step (3) is in a range from 0.53 mol/L to 12.76 mol/L.

According to a third aspect, the present invention provides a method for isolating proteins using the biomagnetic microsphere according to the first aspect of the invention, comprising a plurality of steps, including:

(1) adding a binding buffer to the biomagnetic microsphere and mixing well, magnetically separating the biomagnetic microsphere, adding the separated biomagnetic microsphere to a solution containing a protein to be isolated, before mixing well and having incubated therein, to obtain a biomagnetic microsphere E to which the target protein binds;

(2) performing a solid-liquid separation before removing a supernatant, washing the biomagnetic microsphere E with a washing solution, and eluting the biomagnetic microsphere E with an eluent, collecting a supernatant;

(3) isolating and purifying the target protein from the supernatant.

According to a fourth aspect, the present invention provides a plurality of applications of the biomagnetic microsphere according to the first aspect of the invention, including protein isolation and purification, immunoassay, target antibody drug enrichment, targeted drug delivery, nucleic acid separation and extraction, cell sorting, enzyme immobilization, gene vector construction, and so on.

A plurality of main advantages and beneficial effects of the present invention are as follows:

(1) the prepared biomagnetic microsphere can capture a big amount of the target protein from a mixed system onto the biomagnetic microsphere efficiently, achieving a high-throughput binding of the target protein;

(2) the prepared biomagnetic microsphere can implement an efficient elution of the target protein and effectively reduce the retention time and the retention ratio of the target protein during a process of the elution;

(3) it is easy to operate and use the prepared biomagnetic microsphere. In particular, it is possible to control a position and an aggregation state of the biomagnetic microsphere efficiently simply by using a small piece of magnet, and achieve a rapid dispersion and aggregation of the biomagnetic microsphere in a solution, making protein isolation and purification easier and faster without requiring an expensive large-scale experimental facility, for example, a high-speed centrifuge;

(4) The prepared biomagnetic microsphere can be widely used, including an immunoassay, a rapid isolation and purification of a target protein such as a His-tagged protein, target antibody drug enrichment, targeted drug delivery, nucleic acid separation and extraction, cell sorting, enzyme immobilization, gene vector construction.

(5) it is possible to adjust a plurality of characters of the prepared magnetic microsphere including a water solubility, a size in a solution, a suspension property by controlling a dimension of the magnetic microsphere body and coupling a plurality of polymers having different water solubility to the surface of the magnetic microsphere according to the present invention;

(6) the biomagnetic microsphere provided by the present invention can suspend stably in an aqueous liquid, maintaining for 2 days or longer before being sunken. Further, the biomagnetic microsphere is able to suspend stably in an aqueous liquid system without a continuous stirring, which is an excellent performance brought by a unique structural design. On one hand, the size of the magnetic microsphere body thereof can be disposed to be below 10 microns, or even below 1 micron; on another hand, it is possible to coat a hydrophilic polymer onto the outer surface of the magnetic microsphere body, and adjust a grafting density of the polymer on the outer surface of the magnetic microsphere body, as well as adjusting a plurality of characters including hydrophilicity thereof, a structure type, a hydrodynamic radius, a chain length, a branched chain number, a branched chain length and more, so as to better control a suspension state of the biomagnetic microsphere in a system.

DETAILED DESCRIPTION

Figure 1:
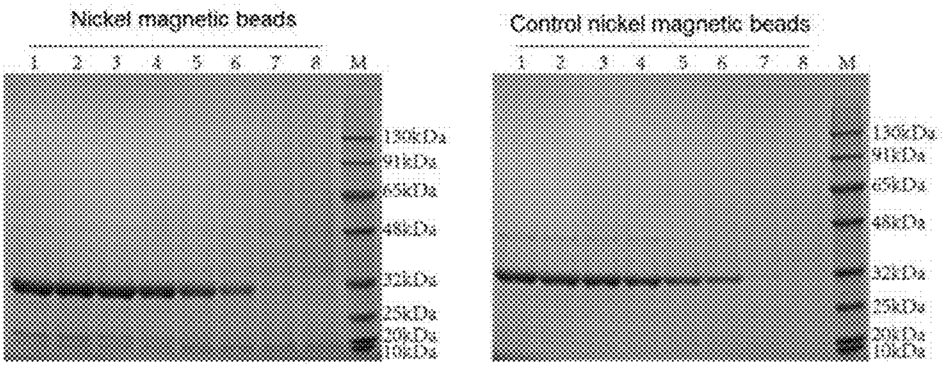
FIG. 1 shows diagrams of electrophoresis detection with SDS-PAGE. Images on the left and right sides respectively show comparison between two purification results of a biomagnetic microsphere of the present invention (i.e., nickel magnetic beads, also known as KM magnetic beads) and a microsphere in a control group (control nickel beads).

The present invention will be further illustrated below in combination with specific examples and embodiments. It should be understood that these examples and embodiments are provided solely for the purpose of illustration and should not to be regarded as limitations to the scope of the present invention. With respect to the experimental methods without specifically described conditions in the following examples, one person may preferably follow and refer to conditions guided by the specific examples described above, and follow conventional conditions, such as conditions described in Sambrook et. al, Molecular Cloning: A Laboratory Manual (New York: Cold Spring Harbor Laboratory Press, 1989), "A Laboratory Manual for Cell-Free Protein Synthesis", "Edited by Alexander S. Spirin and James R. Swartz. Cell-free protein synthesis: methods and protocols[M]. 2008", or follow the conditions recommended by the manufacturer.

Unless otherwise stated, percentage and portions in the present invention refer to percentage by weight and portions by weight, respectively. Unless otherwise stated, materials and reagents used in the examples of the present invention are all commercially available products. Unless otherwise stated, temperatures in the present application are given in degree Celsius (° C.).

Terms

Substances include, but are not limited to, molecules, molecular aggregates, molecular conjugates, molecular complexes and other forms.

Targets refer to the substance to be bound by the biomagnetic microsphere of the present invention, preferably biomolecules or bioactive substances. For example, they include but are not limited to proteins (e.g., antibodies, antigens, antibiotics, interleukins, etc.), protein complexes, protein conjugates (e.g., glycoprotein), nucleic acid molecules (e.g., DNA, RNA, etc.), protein and nucleic acid conjugates or complexes, viruses, cells, liposomes, vesicles, and other substances. The biomagnetic microsphere of the present invention can be combined with the target through the functional groups contained in the branched chain of the linear polymer, thereby achieving isolation and purification of the targets. In the present invention, the targets are preferably protein substances. The protein substances may be proteins or substances including a protein structure, for example, including but not limited to protein complexes, protein conjugates, protein and nucleic acid conjugates or complexes. The protein conjugates are formed by covalent bonds, dynamic covalent bonds, supramolecular forces (e.g., hydrogen bonds) and other means. The protein complexes are formed by complexation.

Target protein and the target of the protein refer to a protein substance.

A His-tagged label can be used as a target, and refers to a substance carrying His tag (histidine tag); carrying of the His tag can be achieved by connection methods, including but not limited to covalent bonds, dynamic covalent bonds, supramolecular interactions, as long as the connection between the His tag and the labeled part is stable when the target is captured by the His tag, and the His-tagged label can exist stably as a whole during the capture process.

In the present invention, proteins and proteins have the same meaning and can be used interchangeably. Fusion protein is also a kind of protein. In a broad sense, the protein of the present invention includes polypeptides. Any protein involved in the present invention, unless otherwise specified (such as specifying a specific sequence), should be understood to also include its derivatives.

Protein derivatives: the protein derivatives comprise at least C-terminal tags, N-terminal tags, C-terminal and N-terminal tags, wherein C-terminal refers to the COOH-terminal, and N-terminal refers to the $NH_2$-terminal, as commonly understood by those skilled in the art. The tag can be a polypeptide tag or a protein tag. The protein derivatives may also comprise their products from the chemical modification method, including but not limited to salt forms, complexes, ester compounds, substitution products, etc. The chemical modification method comprises, for example, ionization, salinization, desalination, complexation, decomplexation, chelation, dechelation, addition reaction, substitution reaction, elimination reaction, insertion reaction, oxidation reaction, reduction reaction, post-translational modification, etc. In particular, the method comprises oxidation, reduction, methylation, demethylation, amination, carboxylation, and vulcanization, for example.

Magnetic microspheres or microspheres with a small particle size that can be strongly magnetized, can also be described as magnetic beads. Preferably, they have a diameter in a range from 0.1 μm to 1000 μm.

Magnetic microsphere body: $SiO_2$-coated magnetic particles, such as $SiO_2$-coated $Fe_3O_4$ particles.

Magnetic microsphere A: an amino-modified magnetic microsphere.

Magnetic microsphere B: a magnetic microsphere containing a carbon-carbon double bond.

Magnetic microsphere C: a magnetic microsphere modified by acrylic polymers.

Magnetic microsphere D: a biomagnetic microsphere complexed with nickel ions obtained by using the magnetic microsphere C.

Magnetic microsphere E: the product of the magnetic microsphere D combined with the target (e.g., protein), that is, a magnetic microsphere containing the captured material.

KM magnetic beads: sodium polyacrylate magnetic beads obtained by polymerization reaction using sodium acrylate as a monomer molecule. The sodium polyacrylate magnetic beads have a basic structure consistent with the basic structure of the polyacrylic acid magnetic beads partially synthesized in the example. When preparing the polyacrylic acid magnetic beads, acrylic acid is used as the monomer molecule for polymerization.

Linear polymer and linear polymers have the same meaning and can be used interchangeably.

Acrylic polymer: refers to a homopolymer or copolymer having a —C(COO—)—C— unit structure. The copolymerization form of the copolymer is not particularly limited, as long as it can provide a linear backbone and a metered side group COO—, as appropriate. Other substituents are allowed to be present on the carbon-carbon double bonds, as long as they do not affect the progress of the polymerization reaction, such as methyl substituents (corresponding to —$CH_3C$(COO—)—C—). COO— can be in the form of —COOH, or in the form of a salt (e.g., sodium salt), or in the form of formate (preferably an alkyl formate, such as methyl formate-$COOCH_3$, ethyl formate-$COOCH_2CH_3$; it can also be hydroxyethyl formate-$COOCH_2CH_2OH$). The specific structural forms of —C(COO—)—C—unit structure include but are not limited to —CH(COOH)—$CH_2$—, —CH(COONa)—$CH_2$—, —MeC(COOH)—$CH_2$—, —MeC(COONa)—$CH_2$—, —CH($COOCH_3$)—$CH_2$—, —CH($COOCH_2CH_2OH$)—$CH_2$—, —MeC($COOCH_3$)—$CH_2$—, —MeC($COOCH_2CH_2OH$)—$CH_2$—, and a combination thereof. Me is methyl. Only one of the above unit structures (corresponding to homopolymers), or two or more unit structures (corresponding to copolymers) can be present on the linear backbone of a polymer molecule.

Acrylic monomer molecules: refer to monomer molecules that can be used to synthesize the above-mentioned acrylic polymers and have the basic structure of C(COO—)═C, for example, CH(COOH)═$CH_2$, CH(COONa)═$CH_2$, $CH_3C$(COOH)═$CH_2$, $CH_3C$(COONa)═$CH_2$, CH($COOCH_3$)═$CH_2$, CH($COOCH_2CH_2OH$)═$CH_2$, $CH_3C$($COOCH_3$)═$CH_2$, $CH_3C$($COOCH_2CH_2OH$)═$CH_2$, etc.

Branched chain: the branched chain and the side branched chain have the same meaning and can be used interchangeably. In the present invention, the branched chain refers to a side chain or a side group bonded on the backbone of the linear polymer. There is no special requirement for the length and size of the branched chain. The branched chain may be a short branched-chain, for example, carboxyl, hydroxyl and amino, or it may be a long branched-chain with a large number of atoms. The structure of the branched chain is not particularly limited. It may be linear or a branched chain having a branched structure. The branched chain may also contain additional side chains or side groups. Structure features of the branched chain, for example, number, length, size and the degree of rebranching, are selected so that a flexible swing of the linear backbone can be achieved, so that a network structure is not formed and the branched chains are not stacked, thus the retention ratio is not increased. The branched chains on the backbone can be spaced apart from each other at an adjustable distance.

Purification medium refers to a functional element used to specifically capture a target. The purification medium of the biomagnetic microsphere of the present invention is located at the branched chain of the linear polymer coupled to the outer surface of the magnetic microsphere body.

Group: it can be a single atom, or a group of atoms, it can be in the form of a free radical, or it can be in the form of an ion.

Functional group of a polymer branched chain: it features reaction activity or has reactive activity after being activated. It is capable of directly interacting with active groups of other substances, or capable of interacting with active groups of other substances after being activated, so that the other substances bind to the branched chains of the polymer. One of the preferred forms of the functional group of the polymer branched chain is a specific binding site. The other substance can be a purification medium or a target to be captured.

Binding: it can be covalent or non-covalent binding, including but not limited to covalent binding, dynamic covalent binding, supramolecular interaction, etc. The supramolecular interactions include, but are not limited to, hydrogen bonds, some specific binding effects, etc.

Specific binding site: in the present invention, the specific binding site refers to a group or a structural part with a binding function at the branched chain of the polymer. The group or the structural part can achieve specific recognition or binding of a certain target. The specific binding can be achieved through coordination, complexation, electrostatic force, van der Waals force, hydrogen bonds, covalent bonds, etc.

Washing solution: eluting impurities such as impure proteins; after being eluted, the impure proteins are removed with the washing solution.

Flow-through solution: it refers to the penetrating solution obtained after it is incubated by purified magnetic beads and separated therefrom. The solution contains the residual target not separated. For example, the flow-through solution may refer to the solution that is added to the affinity column and penetrates through the column, such as flow-through solution 1, flow-through solution 2, and flow-through solution 3, which represents solution penetrating through the column for the first time, solution penetrating through the column for the second time, and solution penetrating through the column for the third time, respectively.

Eluent: elute the target protein; after elution, the target protein exists in the eluent.

Binding capacity: for example, a capacity for allowing the magnetic microsphere to bind to a protein.

Affinity: refers to the substrate concentration at which the magnetic microspheres only bind to 50% of the substrate by using the substrate solution having different concentration grades.

PNA: peptide nucleic acid, is a DNA analog in which the glycosylsugar phosphate backbone is replaced by the polypeptide backbone. It is a nucleic acid sequence specific reagent, first invented by Danish organic chemist Ole Buchardt and biochemist Peter Nielsen in 1980s. It is a third-generation antisense reagent which is constructed by computer design and is finally artificially synthesized, based on the first-generation and the second-generation antisense reagents. It is a brand new DNA analog. In particular, the backbone of the pentose phosphodiester bond in DNA is replaced with neutral peptide chain amide 2-aminoethylglycine bond, and the rest of the structure is the same as that of DNA. PNA can recognize and bind DNA or RNA sequences through Watson-Crick base pairing to form a stable double helix structure. Since PNA has no negative charge, and no electrostatic repulsion is not found between it and DNA or RNA, the stability and specificity of the binding are greatly improved; PNA-DNA hybridization or PNA-RNA hybridization are different from DNA-DNA hybridization or DNA-RNA hybridization, wherein the former is almost not affected by the salt concentration of the hybridization system. In addition, the hybridization ability of PNA with DNA or RNA molecules is much better than that of DNA/DNA or DNA/RNA. It exhibits high hybridization stability, excellent ability to recognize specific sequences, and it is not hydrolyzed by nucleases and proteases. It can also be linked with ligand and co-transfected into cells. The above-mentioned advantages are not available in other oligonucleotides. In view of the above-mentioned advantages that many DNA molecules do not possess, over the past ten years, people have found applications for PNA in many high-tech fields.

eGFP: Enhanced Green Fluorescent Protein.

RFU: Relative Fluorescent Unit.

RLU: Relative Light Unit

Solution X: an aqueous solution containing 2-morpholineethanesulfonic acid (CAS: 4432-31-9) at a final concentration of 0.01-1 mol/L and NaCl at a final concentration of 0.1-2 mol/L.

Solution Y: PBS buffer solution with pH 7.2-7.5, such as an aqueous solution containing disodium hydrogen phosphate at a final concentration of 0.0684 mol/L, sodium dihydrogen phosphate at a final concentration of 0.0316 mol/L, and sodium chloride at a final concentration of 0.15 mol/L.

In the present invention, "preferably (for example, prefer, preferable, preferably, preferred, etc.)", "more preferably", "better", "most preferably" and other preferred embodiments are illustrated for providing some embodiments instead of posing any limitations to the scope and embodiments of the present invention.

Throughout the description of the present invention, "one of the preferred", "one of the preferred embodiments", "one of the preferred embodiments", "preferred examples", "in a preferred embodiment", "in some preferred embodiments", "preferably", "preferable", "more preferably", "most preferably", "further preferably" and other preferred methods, as well as "one of the embodiments", "one of the methods", "example", "specific example", "for example", "for instance", "such as" and other illustrative enumeration methods, do not limit the scope of the invention, and specific features described in the embodiments are included in at least one embodiments of the invention. In the present invention, the specific features described in the embodiments can be combined in any one or a plurality of embodiments in any suitable manner. In the present invention, technical solutions for respective preferred embodiments can also be combined in any suitable manner.

"Optically" means something is not essential, which depends on whether it can implement the technical solution of the present invention. In the present invention, "optical manner" means that it can be used to implement the invention as long as it is suitable for the technical solution of the invention.

In the present invention, "a combination thereof" and "any combinations thereof" all refer to any suitable combination of the aforementioned listed objects, as long as those combinations can achieve the purpose of the invention. The scope covered by the above definition includes but is not limited to expressions such as "or a combination thereof", "or a combination thereof", "and a combination thereof", "and combinations thereof", etc. In the present invention, "any combination thereof" means the number of the combination is "greater than 1", and represents the following groups in coverage: "any one, or a group consisting of at least two of".

In the present invention, "one or more", and "at least one", "a combination thereof", "or a combination thereof", "and combinations thereof", "or any combinations thereof", "and any combinations thereof" have the same meaning and can be used interchangeably, representing the quantity is equal to "1" or "greater than 1".

In the present invention, the use of "or/and", "and/or" means "any one of them or any combination thereof", and also means at least one of them.

In the present invention, the technical means in the prior art described by the terms "usually", "conventional", "generally", "always" are also cited as references for the content of the present invention. Unless otherwise specified, the technical means modified by those terms can be regarded as one of the preferred embodiments of some technical features. However, it should be noted that they do not limit the range and the scope of the invention.

IVTT system: in vitro transcription and translation system, it is a cell-free protein synthesis system (or called an in vitro protein synthesis system) using exogenous DNA as a template. Using exogenous mRNA or DNA as the template for protein synthesis, the cell-free protein synthesis system can achieve the synthesis of the target proteins by artificially controlling the addition of substrates and transcription and translation-related protein factors required for protein synthesis. The cell-free protein synthesis system of the present invention is not particularly limited, and it can be one or any combination of the cell-free protein synthesis system based on the following cell extract: yeast cell extract, *Escherichia coli* cell extract, mammal cell extract, plant cell extract, or insect cell extract. It should be noted that the in vitro protein synthesis system of the present invention does not exclude the presence of intact cells, and allows an extremely small amount or a small amount of intact cells to be included therein, however, it preferably does not contain the intact cells.

It should be understood that the above-mentioned technical features of the present invention and the technical features specifically described hereinafter (such as in Examples) can be combined with each other to form a new or preferred technical solution without departing from the scope of the invention, as long as the technical solution of the present invention can be achieved. For the sake of brevity, details will not be repeated herein.

According to a first aspect, the present invention provides a biomagnetic microsphere, wherein the biomagnetic microsphere has a magnetic microsphere body, an outer surface of the magnetic microsphere body has at least one liner polymer with a branched chain; one end of the linear polymer with the branched chain is covalently coupled to the outer surface of the magnetic microsphere body, and other parts are free on the outer surface of the magnetic microsphere body, a backbone of the linear polymer is a polyolefin backbone; preferably, no cross-linking agent is required in a backbone forming process of the linear polymer.

The linear polymer contains at least one linear backbone, and each linear backbone carries at least three branched chains containing functional groups, that is, each linear backbone carries at least three functionalized branched chains; the linear polymer contains at least three functional groups. In the present embodiment, the polymer not only has the high flexibility of the linear backbone, but also has the advantage of high magnification of the number of the branched chains, thus, a high-speed and high-throughput binding, and a high-efficient and high ratio (high yield) separation can be achieved.

In order to construct the magnetic microsphere body, it is preferable to select magnetic particles and have the magnetic particles coated with silica. The magnetic particles contain magnetic materials or magnetic components, the magnetic particles have a chemical component comprising at least one selected from the group consisting of iron compounds (e.g., iron oxides), iron alloys, zinc oxides, manganese oxide mixture, gadolinium oxide mixture, cobalt compounds (e.g., cobalt oxides), nickel compounds (e.g., nickel oxides), nickel alloys, manganese oxides, manganese alloys, zinc oxides, gadolinium oxides, and chromium oxides, that is, one or more of the components, that is, any one of them or any combinations thereof.

In one of the preferred embodiments, the magnetic particles have a chemical component comprising one selected from the group consisting of iron oxide, iron, cobalt, $Co^{2+}$, iron nitride, $Mn_3O_4$, GdO, nickel, $Ni^{2+}$, and any combinations thereof; wherein, the iron oxide is preferably magnetite ($Fe_3O_4$), maghemite ($\gamma$-$Fe_2O_3$), or a combination of these two oxides, more preferably, iron oxide is $Fe_3O_4$.

In another one of the preferred embodiments, the magnetic particles have a chemical component comprising one selected from the group consisting of $Fe_3O_4$, $\gamma$-$Fe_2O_3$, iron nitride, $Mn_3O_4$, AlNi(Co), FeCr(Co), FeCrMo, FeAlC, AlNi (Co), FeCrCo, ReCo, ReFe, PtCo, MnAlC, CuNiFe, AlMnAg, MnBi, FeNi(Mo), FeSi, FeAl, FeNi(Mo), FeSiAl, $BaO\cdot6Fe_2O_3$, $SrO\cdot6Fe_2O_3$, $PbO\cdot6Fe_2O_3$, GdO, and a combination thereof; wherein Re is rhenium, a rare earth element. Mo is molybdenum.

The size (such as volume) of the magnetic microsphere body of the present invention is not particularly limited, and can be any feasible particle size, but preferably the diameter of the magnetic microsphere body is in a range from 0.1 μm to 1000 μm. Unless otherwise specified, the diameter size refers to the average size. For example, it is in a range from 1 μm to 1000 μm, specifically, for example, 1 μm, 10 μm, 100 μm, 200 μm, 500 μm, 800 μm, and 1000 μm; one of the preferred diameter of the invention is 1 μm.

For the biomagnetic microsphere, the smaller particle size helps the protein solid system to be suspended in the protein synthesis reaction system, and it can be more fully contact with the protein expression product, so that the protein product is captured in a more efficient way and the binding rate (binding efficiency) is improved.

In some preferred embodiments, the magnetic microsphere body has a diameter in a range from 0.1 μm to 10 μm.

In some preferred embodiments, the magnetic microsphere body has a diameter in a range from 0.2 μm to 6 μm.

In some preferred embodiments, the magnetic microsphere body has a diameter in a range from 0.4 μm to 5 μm.

In some preferred embodiments, the magnetic microsphere body has a diameter in a range from 0.5 μm to 3 μm.

In some preferred embodiments, the magnetic microsphere body has a diameter in a range from 0.2 μm to 1 μm.

In some preferred embodiments, the magnetic microsphere body has a diameter in a range from 0.5 μm to 1 μm.

In some preferred embodiments, the magnetic microsphere body has a diameter in a range from 1 μm to 1000 μm.

In some preferred embodiments, the magnetic microsphere body has a diameter (the deviation can be ±25%, ±20%, ±15%, ±10%) selected from, or a diameter in a range between any two selected from the group consisting of 0.1 μm, 0.15 μm, 0.2 μm, 0.25 μm, 0.3 μm, 0.35 μm, 0.4 μm, 0.45 μm, 0.5 μm, 0.55 μm, 0.6 μm, 0.65 μm, 0.7 μm, 0.75 μm, 0.8 μm, 0.85 μm, 0.9 μm, 0.95 μm, 1 μm, 1.5 μm, 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm.

The formed magnetic microsphere body and the magnetic microsphere containing the magnetic microsphere body, on the one hand, can be quickly positioned, guided and separated under the action of an external magnetic field, and on the other hand, can confer active functional groups, for example, hydroxyl, carboxyl, aldehyde group, amino group, nickel ion, to the outer surface of the magnetic microsphere body or the magnetic microsphere by surface modification or chemical polymerization, etc. In addition, the magnetic microsphere body or magnetic microsphere can bind to biologically active substances such as antibodies, cells, DNA and so on through covalent bonds, non-covalent bonds and other ways.

The polymer used to couple the magnetic microsphere body may be one or more macromolecule with a carboxyl branched chain selected from the group consisting of polyacrylic acid, polyacrylate, polymethacrylic acid, and polymethacrylate and other polymers.

In one of the preferred embodiments, the linear polymer coupled to the outer surface of the biomagnetic microsphere is obtained by polymerization of one selected from the group consisting of acrylic acid, acrylate, acrylic ester, methacrylic acid, methacrylate, methacrylic ester, etc., and a combination thereof; preferably, no cross-linking agent is required in a polymerization process.

The branched chain of the linear polymer contains a functional group, and the functional group is able to bind to a target object. Preferably, the branched chain of the linear polymer contains a specific binding site (i.e., the functional group is the specific binding site), and the specific binding site can specifically bind to the target object.

Further preferably, the specific binding site is a nickel ion, the nickel ion is able to specifically bind to a label of a His tag (histidine tag).

In one of the preferred embodiments, the functional group of the linear polymer is one selected from the group consisting of carboxyl, hydroxyl, amino, sulfhydryl, and a combination thereof.

In one of the preferred embodiments, the linear polymer is directly fixed to the outer surface of the magnetic microsphere body, or indirectly fixed to the outer surface of the magnetic microsphere body through a linking group.

The formed biomagnetic microsphere can be used to bind active substances. The active substances can be directly bonded or bonded via a linker molecule. The linker molecule can be one selected from the group consisting of nucleic acid molecule, a peptide nucleic acid, a nucleic acid aptamer, deoxyribonucleic acid, ribonucleic acid, leucine zipper, helix-turn-helix motif, zinc finger motif, oligonucleotide, biotin, avidin, streptavidin or anti-hapten antibody, and a combination thereof. Of course, the linker molecule can also be a double-stranded nucleic acid construct, a double helix, a homohybrid or heterohybrid selected from the group consisting of DNA-DNA, DNA-RNA, DNA-PNA, RNA-RNA, RNA-PNA and PNA-PNA.

According to a second aspect, the present invention provides a method for preparing the biomagnetic microsphere according to the first aspect of the invention, comprising a plurality of steps including:

Step (1): providing a magnetic microsphere body, performing a chemical modification to a surface of the magnetic microsphere body, and introducing a reactive group R1;

Step (2): optionally, introducing a functional group R2 by a covalent coupling reaction between the reactive group R1; the functional group R2 can function as a reactive center RC to start the polymerization reaction; if the reactive group R1 in Step (1) can function as the reactive center RC to start the polymerization reaction, this step can be omitted and directly proceed to Step (3); for addition polymerization (radical polymerization, cationic polymerization, anionic polymerization), the reactive center RC is an initiation center; for stepwise polymerization, the reactive center RC can also function as the starting point for the "growth" of the polymer chain;

- the reactive group refers to a group capable of undergoing a coupling reaction and forming a covalent bond;

Step (3): adding a monomer molecule M1, starting the polymerization reaction of the monomer molecule MG by using the reactive center RC as the starting point; the monomer molecule MG comprises at least one monomer molecule MB capable of providing a functionalized branched chain end; the functionalized branched chain end means that the branched chain end is a functional group F1 or can be transformed into the functional group F1 after modification; a chain skeleton of a linear polymer with a branched chain is formed through the polymerization reaction, and a connection point for covalently fixing the linear polymer is formed at the reactive center RC;

- the functional group can form covalent bonds, dynamic covalent bonds, supramolecular interactions and other binding capacity;
- the mechanism of the polymerization reaction is not particularly limited; for example, it can be selected from the group consisting of: radical polymerization, cationic polymerization, anionic polymerization, and stepwise polymerization;
- the monomer molecule MG can be a single type of molecule, and a homopolymerization reaction can be carried out then; it can also be a combination of different types of molecules, and a copolymerization reaction can be carried out then; the monomer molecule MB capable of providing functionalized branched chains is, for example, acrylic monomer molecule (capable of radical polymerization), etc.;

Step (4): binding purification medium to the branched chain end by using a interaction between the purification medium and the functional group F1 at the end of the branched chain, to obtain a biomagnetic microsphere having the structure of "magnetic microsphere body—linear polymer with a branched chain—purification medium".

The above-mentioned steps can be carried out separately, or simultaneously in a suitable combination.

The purification medium refers to a functional element used to specifically capture a target object in the biomagnetic microsphere.

The "interaction between the purification medium and the functional group F1 at the end of the branched chain" is, for example, a covalent bond, a dynamic covalent bond, a supramolecular interaction (e.g., an affinity complex interaction), etc.

The method for preparing the biomagnetic microsphere may comprise a plurality of steps including:

Step (1): providing a magnetic microsphere body, performing a chemical modification to the magnetic microsphere body, by introducing the amino group onto the outer surface of the magnetic microsphere body before forming a magnetic microsphere A;

- in one of the preferred embodiments, the chemical modification to the magnetic microsphere body is carried out with a silane coupling agent;

Step (2): coupling an acrylic acid molecule covalently onto an outer surface of the magnetic microsphere A by using a covalent reaction between carboxyl and the amino group, so as to introduce a carbon-carbon double bond and form a magnetic microsphere B;

Step (3): in absence of the cross-linking agent, polymerizing the acrylic monomer molecules by a polymerization reaction between the carbon-carbon double bond, having an obtained linear polymer covalently coupled to an outer surface of the magnetic microsphere B, before performing a solid-liquid separation and removing a liquid phase to obtain a magnetic microsphere C;

- when the functional group contains the specific binding site, the method further comprises a step of: (4) coupling the specific binding sites at a branched chain of a linear polymer of the magnetic microsphere C.

In one of the preferred embodiments, the acrylic monomer molecule is a sodium acrylate monomer molecule.

In one of the preferred embodiments, the magnetic microsphere is precipitated by a magnet, the liquid phase is removed, and the magnetic microsphere C is obtained after washing.

The Steps (1) and (2) described above can be combined into one step, that is, Step (2) can be omitted. For example, they can be combined into a following Step (I): performing a chemical modification to the magnetic microsphere body by adopting a trimethoxysilanized acrylic molecule, and introducing a carbon-carbon double bond onto the outer surface of the magnetic microsphere body, before forming the magnetic microsphere B. In particular, 3-(methacryloxy) propyltrimethoxysilane (KH570 acyloxysilane, CAS: 2530-85-0) is used to modify the magnetic microsphere body, a carbon-carbon double bond can be introduced to form the magnetic microsphere B, and the carbon-carbon double bond can function as the active center to initiate the polymerization reaction. This modification route is also called KH570 modification route.

In one of the preferred embodiments, the branched chain of the linear polymer of the magnetic microsphere C contains the nickel ion. In the present embodiment, the method further comprises a step of: (4) coupling tricarboxylic amine to the magnetic microsphere C, before complexing $Ni^{2+}$ to three carboxyl groups in a residue of the tricarboxylic amine to obtain a magnetic microsphere D, that is, a target biomagnetic microsphere; wherein the target biomagnetic microsphere can bind to a label of the His tag specifically.

In one of the preferred embodiments, three carboxyl groups in the tricarboxylic amine form a structure of $N(C—COOH)_3$), so that the nickel ion can be complexed.

In one of the preferred embodiments, the tricarboxylic amine is N,N-bis(carboxymethyl)-L-lysine, and the amount of the N,N-bis(carboxymethyl)-L-lysine is preferably in a range from 0.5 g/L to 550 g/L.

In one of the preferred embodiments, the amount of the acrylic acid for preparation of the magnetic microsphere A in Step (2) is in a range from 0.002 mol/L to 20 mol/L.

In one of the preferred embodiments, the amount of the sodium acrylate for preparation of the magnetic microsphere B in Step (3) is in a range from 0.53 mol/L to 12.76 mol/L.

In particular, the invention provides the following technical solution:

(1) $SiO_2$-coated $Fe_3O_4$ magnetic beads are used as the magnetic microsphere body; a coupling agent (e.g., 3-aminopropyltriethoxysilane, APTES, CAS: 919-30-2, an aminated coupling agent and a silane coupling agent, in particular an aminated silane coupling agent) is used to chemically modify the $SiO_2$-coated $Fe_3O_4$ magnetic microsphere body, amino groups are introduced onto the outer surface of the magnetic microsphere body to form a magnetic microsphere A;

(2) acrylic acid molecules are covalently coupled onto the outer surface of the magnetic microsphere by using a covalent reaction between carboxyl and the amino group, so as to introduce a carbon-carbon double bond onto the outer surface of the magnetic microsphere and obtain a magnetic microsphere B, wherein an outer surface thereof is modified with the carbon-carbon double bond;

(3) a linear polymerization of the acrylic monomer molecules (e.g., sodium acrylate monomer molecules) is realized by a polymerization reaction between carbon-carbon double bond; while the polymerization reaction is carried out, a polymerization product is covalently coupled onto the outer surface of the magnetic microsphere, to obtain a magnetic microsphere C, wherein an outer surface thereof is covalently modified with acrylic polymer.

In particular, the invention further provides the following technical solution:

(I) $SiO_2$-coated $Fe_3O_4$ magnetic beads are used as the magnetic microsphere body; a coupling agent (e.g., 3-(methacryloyloxy)propyltrimethoxysilane, CAS: 2530-85-0) is used to chemically modify the $SiO_2$-coated $Fe_3O_4$ magnetic microsphere body, allyl carbon-carbon double bonds are introduced onto the outer surface of the magnetic microsphere body to form a magnetic microsphere B, wherein an outer surface thereof is modified with the carbon-carbon double bond;

(II) a linear polymerization of the acrylic monomer molecules (e.g., sodium acrylate monomer molecules) is realized by a polymerization reaction between carbon-carbon double bond; while the polymerization reaction is carried out, a polymerization product is covalently coupled onto the outer surface of the magnetic microsphere, to obtain a magnetic microsphere C, wherein an outer surface thereof is covalently modified with a acrylic polymer.

The linear polymer formed here has one end covalently coupled to the outer surface of the magnetic microsphere, and the remaining part are free in the solution and can fully contact molecules in the solution, to enhance the capture of the target proteins. The target proteins directly get rid of the constraints from the magnetic microsphere during the process of elution, allowing them to enter the eluate directly. Comparing with polymers physically wound on the outer surface of the magnetic microsphere or integrated with the magnetic microsphere, the covalently immobilized linear polymer can effectively reduce the stacking of molecular chains, strengthen the stretch and swing of the molecular chains in the solution, enhance the capture of the target protein, and reduce the retention ratio and retention time of the target protein during the process of elution.

Taking sodium acrylate as the monomer molecule as an example, the polymerization product is sodium polyacrylate. The backbone of sodium polyacrylate is a linear polyolefin backbone, and a lot of side branched chains COONa are covalently connected along the backbone, the functional group contained in the branched chain is also COONa; the polymerization reaction here does not use cross-linking agent (such as N,N'-methylene bisacrylamide, CAS: 110-26-9), instead, the polymerization product is allowed to produce a linear polymer with a linear backbone without the addition of the cross-linking agent, avoiding the formation of a network polymer in which the molecular chains are cross-linked with each other. If the network polymer in which the molecular chains are cross-linked with each other is formed, and the elution efficiency of the target protein is affected by forming a porous structure.

(4) Taking the magnetic microsphere C obtained by polymerization of sodium acrylate as an example, since reaction is carried out in a slightly acidic system, sodium acrylate is decomposed into sodium ions and acrylic acid ions in the water phase. In the slightly acid system, most of acrylic acid ions become acrylic acid with carboxyl groups. After the linear molecular chain of sodium polyacrylate is covalently cross-linked to the outer surface of the magnetic microsphere, tricarboxylic amine (such as N,N-bis(carboxymethyl)-L-lysine, CAS: 113231-05-3) is covalently coupled to the branched chain of the linear polymer by using the covalent reaction between carboxyl and amino group, and then nickel ions are added to chelate to the three carboxyl groups of N,N-bis(carboxymethyl)-L-lysine, to obtain the biomagnetic microsphere for the isolation and purification of histidine-tagged proteins.

According to a third aspect, the present invention provides a method for isolating proteins using the biomagnetic microsphere according to the first aspect, comprising a plurality of steps including:

(1) adding a binding buffer to the biomagnetic microsphere and mixing well, magnetically separating the biomagnetic microsphere, adding the separated biomagnetic microsphere to a solution containing a protein to be isolated, before mixing well and having incubated therein, to obtain a biomagnetic microsphere E to which the target protein binds;

(2) performing a solid-liquid separation before removing a supernatant, washing the biomagnetic microsphere E with a washing solution, and eluting the biomagnetic microsphere E with an eluent, collecting a supernatant;

in one of the preferred embodiments, the solid-liquid separation is performed by magnetic attraction;

in one of the preferred embodiments, the solid-liquid separation is performed by centrifugation;

(3) isolating and purifying the target protein from the supernatant.

In one of the preferred embodiments, the ratio of the biomagnetic microsphere to the protein solution to be treated is in a range from 1:10 to 1:80 by volume.

In one of the preferred embodiments, the ratio of the biomagnetic microsphere to the protein solution to be treated is in a range from 1:10 to 1:60 by volume.

In one of the preferred embodiments, the ratio of the biomagnetic microsphere to the protein solution to be treated is in a range from 1:10 to 1:50 by volume.

In one of the preferred embodiments, the ratio of the biomagnetic microsphere to the protein solution to be treated is in a range from 1:20 to 1:50 by volume.

In one of the preferred embodiments, the ratio of the biomagnetic microsphere to the protein solution to be treated is in a range from 1:20 to 1:40 by volume.

In some embodiments, the reaction solution after the completion of the in vitro protein synthesis reaction is directly used as the solution containing the proteins to be isolated. For example, after the completion of the IVTT reaction (in vitro transcription and translation reaction), the IVTT reaction solution obtained is used as the solution containing the proteins to be isolated.

In some preferred embodiments, various factors required by the in vitro protein synthesis system are exogenously added, separately or in combination, referring to, for example, the PURE system in Japan (e.g., PURExpress kit).

In some preferred embodiments, the in vitro protein synthesis system comprises:

(a) cell extract; preferably, yeast cell extract;

(b) any suitable crowding agent, for example, polyethylene glycol;

(c) optional exogenous sucrose; and (d) optional solvent, wherein the solvent is water or aqueous solvent.

The term "optional" in components (c) and (d) can be independently dispensable.

In a preferred embodiment, the in vitro protein synthesis system according to the present invention comprises yeast cell extract, trihydroxymethyl aminomethane (Tris), potassium acetate, magnesium acetate, nucleoside triphosphate mixtures (NTPs), amino acid mixtures, potassium phosphate, amylase, polyethylene glycol, maltodextrin, etc. Nucleic acid templates encoding the target proteins, such as fluorescent protein DNA, etc., can be further added to the in vitro protein synthesis system for in vitro protein synthesis reactions.

Nucleic acid templates (e.g., DNA encoding fluorescent proteins) can be further added to the in vitro protein synthesis system for in vitro protein synthesis reaction to obtain a reaction solution containing the target proteins. Preferably, the target protein contains a purification tag; when the target protein contains a histidine purification tag, it can specifically bind to nickel ions, so that the biomagnetic microsphere of the present invention can be used for isolation and purification.

In the present invention, the proportion of the yeast cell extract in the in vitro cell-free protein synthesis system is not particularly limited. Generally, the content by volume of the yeast cell extract is in a range of 20%-70% (v/v), preferably, in a range of 30%-60% (v/v), more preferably, in a range of 40%-50% (v/v), further for example, 50% (v/v), based on the total volume of the in vitro cell-free protein synthesis system.

In the present invention, the cell extract preferably does not contain intact cells. Suitable reported cell extract preparation techniques can be selected to prepare the cell extract. The preparation of the cell extract usually comprises at least the following steps of: providing an appropriate amount of yeast cells, breaking the cells, performing solid-liquid separation, and collecting the supernatant. The extraction product obtained according to the preparation method of the cell extract may have a small or an extremely small amount of intact cells left, and this type of extraction product also falls within the scope of the cell extract of the present invention. The cell extract does not exclude the presence of intact cells.

Likewise, the in vitro protein synthesis system does not exclude the presence of intact cells when comprising cell extracts. There are many factors behind the presence of those intact cells. The intact cells may be residues from the process of preparing the cell extract; or they may be introduced intentionally, for example, they may be cell fragments obtained by simple fragmentation of cells added, the cell fragments may be a mixture of the completely fragmented product and the intact cells; or they are intact cells which are added individually.

Typical cell extract (including yeast cell extract) comprises ribosome, tRNA, aminoacyl tRNA synthetase for protein translation, initiation factors, elongation factors and termination release factors required for protein synthesis. Furthermore, the yeast extract (including yeast cell extract) further comprises some other proteins derived from the cytoplasm, especially soluble proteins.

In some preferred embodiments, the yeast cell extract is *Kluyveromyces* cell extract. In some preferred embodiments, the *Kluyveromyces* is one selected from the group consisting of *Kluyveromyces lactis* (*K. lactis*), *Kluyveromyces lactis* vat *drosophilarum, Kluyveromyces lactis* vat *lactis, Kluyveromyces marxianus, Kluyveromyces marxianus* vat *lactis, Kluyveromyces marxianus* vat *marxianus, Kluyveromyces marxianus* vat *vanudenii, Kluyveromyces dobzhanskii, Kluyveromyces aestuarii, Kluyveromyces nonfermentans, Kluyveromyces wickerhamii, Kluyveromyces thermotolerans, Kluyveromyces fragilis, Kluyveromyces hubeiensis, Kluyveromyces polysporus, Kluyveromyces siamensis, Kluyveromyces yarrowii*, and a combination thereof.

Any protein component (e.g., RNA polymerase), required by the in vitro protein synthesis system, can be added in an endogenous way or in an exogenous way. The protein component being added in the endogenous way means that it can be added as one of the components of the cell extract; the protein component being added in the exogenous way means that it is provided in the form of a non-cellular extract, and it can be a single substance or a combination of two or more substances. When added in the exogenous method, it is preferably a purified product of one, two or more substances. When the protein composition is provided in the endogenous way, it is allowed to refer to genetic modification methods provided in the following existing documents and cited documents, including but not limited to: CN108690139A, CN109423496A, CN106978439A, CN110408635A, CN110551700A, CN110093284A, CN110845622A, CN110938649A, CN2018116198190, "Molecular and Cellular Biology, 1990, 10(1):353-360". Those methods include, but are not limited to, inserting coding sequences into intracellular episomal plasmids, integrating coding genes into cell genome, or a combination thereof. When it is provided in the exogenous way, the content of the protein compositions can be controlled and adjusted as required by the system.

In some preferred examples, the in vitro cell-free protein synthesis system comprises: yeast cell extract, Tris, potassium acetate, magnesium acetate, nucleoside triphosphate mixtures (NTPs), amino acid mixtures, potassium phosphate, sugar (any one of glucose, sucrose, maltodextrin and a combination thereof, and when maltodextrin is contained, amylase is also preferably contained), polyethylene glycol, RNA polymerase, etc. The RNA polymerase can be provided endogenously or added exogenously. One of the more preferred forms of the RNA polymerase is T7 RNA polymerase.

In some preferred embodiments, the in vitro cell-free protein synthesis system comprises exogenously added RNA polymerase.

In some preferred embodiments, the in vitro cell-free protein synthesis system comprises exogenously added T7 RNA polymerase.

In some preferred embodiments, the in vitro cell-free protein synthesis system comprises *Kluyveromyces lactis* cell extract and exogenously added T7 RNA polymerase. In some preferred embodiments, the concentration of the T7 RNA polymerase is in a range from 0.01 mg/mL to 0.3 mg/mL. In some other preferred embodiments, the concentration of the T7 RNA polymerase is in a range from 0.02 mg/mL to 0.1 mg/mL. In some further preferred examples, the concentration of the T7 RNA polymerase is in a range from 0.027 mg/mL to 0.054 mg/mL. In some further preferred examples, the concentration of the T7 RNA polymerase is 0.04 mg/mL.

In the present invention, the protein content of the yeast cell extract is preferably in a range from 20 mg/mL to 100 mg/mL, more preferably in a range from 50 mg/mL to 100 mg/mL. The method for measuring the protein content is Coomassie brilliant blue assay.

The mixture of nucleoside triphosphates in the in vitro cell-free protein synthesis system preferably comprises adenosine triphosphate, guanosine triphosphate, cytidine triphosphate, and uridine triphosphate. In the present invention, concentration of each single nucleotide is not particularly limited. In one of the preferred embodiments, the concentration of each single nucleotide is in a range from 0.5 mM to 5 mM, preferably in a range from 1.0 mM to 2.0 mM.

The amino acid mixture in the in vitro cell-free protein synthesis system may comprise natural or unnatural amino acids, and may include amino acids of D-type or amino acids of L-type. Representative amino acids include, but are not limited to, 20 types of natural amino acids: glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine, and histidine. The concentration of each amino acid, preferably, is in a range from 0.01 mM to 0.5 mM, more preferably, in a range from 0.02 mM to 0.2 mM, such as 0.05 mM, 0.06 mM, 0.07 mM, and 0.08 mM.

In some preferred embodiments, the in vitro cell-free protein synthesis system further comprises polyethylene glycol (PEG) or analogs thereof. The concentration of polyethylene glycol or analogs thereof is not particularly limited. Generally, the concentration (w/v) of polyethylene glycol or analogs thereof is in a range from 0.1% to 8%, preferably from 0.5% to 4%, more preferably from 1% to 2%, based on the total weight or volume of the protein synthesis system. Representative examples of PEG include, but are not limited to, PEG3000, PEG8000, PEG6000 and PEG3350. It should be understood that the system according to the present invention may further comprise polyethylene glycol with other various molecular weights (such as PEG 200, 400, 1500, 2000, 4000, 6000, 8000, 10000 and so on).

In some preferred embodiments, the in vitro cell-free protein synthesis system further comprises sucrose. The concentration (w/v) of sucrose is not particularly limited. Generally, the concentration of sucrose is in a range from 0.2% to 4%, preferably from 0.5% to 4%, more preferably from 0.5% to 1%, based on the total volume of the protein synthesis system.

In addition to the yeast extract, some preferred in vitro cell-free protein synthesis systems further comprise the following components: 22 mM Tris (pH 8), 30-150 mM potassium acetate, 1.0-5.0 mM magnesium acetate, 1.5-4 mM nucleoside triphosphate mixture, 0.08-0.24 mM amino acid mixture, 20-25 mM potassium phosphate, 0.001-0.005 mg/mL amylase, 1%-4% (w/v) polyethylene glycol, 320-360 mM maltodextrin (based on the molar amount of glucose unit), 8-25 ng/μL fluorescent protein DNA, etc. Furthermore, the total volume of the in vitro cell-free protein synthesis system is in a range from 10 μL to 10000 μL, preferably in a range from 15 μL to 100 μL, preferably 30 μL. The yeast extract is preferably *Kluyveromyces* cell extract, and more preferably *Kluyveromyces lactis* cell extract.

In addition to the yeast extract, some preferred in vitro cell-free protein synthesis systems further comprise the following components: 22 mM Tris (pH 8), 30-150 mM potassium acetate, 1.0-5.0 mM magnesium acetate, 1.5-4 mM nucleoside triphosphate mixture, 0.08-0.24 mM amino acid mixture, 20-25 mM potassium phosphate, 0.001-0.005 mg/mL amylase, 1%-4% (w/v) polyethylene glycol, 320-360 mM maltodextrin (based on the molar amount of glucose unit), 0.027-0.054 mg/mL T7 RNA polymerase (endogenous, exogenous, or a combination thereof), etc. Those components can be mixed with 8-25 ng/μL fluorescent protein DNA for in vitro protein synthesis reaction. The reaction volume, in one of the preferred embodiments, is in a range from 15 μL to 300 μL. The reaction volume, in one of the preferred embodiments, is in a range from 15 μL to 100 μL. One of the preferred reaction volume is 30 μL.

According to a fourth aspect, the present invention provides a plurality of applications of the biomagnetic microsphere according to the first aspect for protein isolation and purification, immunoassay, target antibody drug enrichment, targeted drug delivery, nucleic acid separation and extraction, cell sorting, enzyme immobilization, gene vector construction.

Example 1 Synthesis of Biomagnetic Microsphere

1.1. Preparation Procedure

Specifically, 0.5-1000 mL (20%, v/v) aqueous solution of $SiO_2$-coated $Fe_3O_4$ magnetic microspheres was measured, the magnetic microspheres were washed with anhydrous ethanol, and 10-300 mL ethanol solution (5%~50%, v/v) of 3-aminopropyltriethoxysilane (APTES, CAS: 919-30-2) was added to the cleaned magnetic microspheres and reacted for 2-72 hours, the magnetic microspheres were washed with anhydrous ethanol and distilled water to obtain magnetic microspheres A, which were amino-modified magnetic microspheres.

0.0001-1 mol acrylic acid was moved into solution X (an aqueous solution containing 2-morpholineethanesulfonic acid (MES, CAS: 4432-31-9) at a final concentration of 0.01-1 mol/L and NaCl at a final concentration of 0.1-2 mol/L)), 0.001-0.5 mol 1-Ethyl-3-(3'-dimethylaminopropyl) carbodiimide hydrochloride (EDC·HCl, CAS: 25952-53-8) and 0.001-0.5 mol N-hydroxysuccinimide (NHS, CAS: 6066-82-6) were added to the solution X, and the obtained mixture was reacted for 3-60 minutes, the above-mentioned solution was added to PBS buffer solution containing 0.5-50 mL magnetic microspheres A and reacted for 1-48 hours, the magnetic microspheres were washed with distilled water to obtain magnetic microspheres B, the outer surface thereof is modified with carbon-carbon double bonds.

0.5-200 mL 5-30% (w/v) sodium acrylate solution was added to 0.5-50 mL magnetic microspheres B, and then 10 uL-20 mL 2%-20% (w/v) ammonium persulfate solution and 1 uL-1 mL tetramethylethylenediamine were added to the solution, then the mixture was reacted for 3-60 minutes, and the magnetic microspheres were washed with distilled water to obtain magnetic microspheres C.

0.5-50 mL magnetic microspheres C were transferred to solution X, 0.001-0.5 mol 1-(3-dimethylaminopropyl)-3-ethylcarbodiimide hydrochloride (EDC·HCl) and 0.001-0.5 mol N-hydroxysuccinimide (NHS) were added to the solution X, after the mixture was reacted for 3-60 minutes, solution Y with 0.0001-1 mol N,N-bis(carboxymethyl)-L-lysine (CAS: 113231-05-3, a tricarboxylic amine) dissolved was added to and reacted for 1-48 hours, 0.0001-1 mol nickel sulfate solid particles were added to the reaction system and reacted for 5 minutes to 24 hours, the magnetic microspheres were washed with distilled water to obtain magnetic microspheres D, that is, the biomagnetic microsphere of the present invention, which uses nickel ions as the purification medium and has the ability to isolate and purify the label that specifically binds to His tag.

1.2. Specific Preparation Method

Wherein, a preferred embodiment for synthesis of the biomagnetic microsphere is as follows: 50 mL aqueous solution (solid content is 20% (v/v)) of $SiO_2$-coated $Fe_3O_4$ magnetic microspheres (having a particle size of 1 μm) was measured, the magnetic microspheres were precipitated by a magnet, the liquid phase was removed, the magnetic microspheres were washed with 60 mL anhydrous ethanol each time for a total of 5 times. 100 mL ethanol solution (25%, v/v) of 3-aminopropyltriethoxysilane (APTES, CAS: 919-30-2) was added to the cleaned magnetic microspheres and mechanically stirred for 48 hours in a water bath at 50° C., then it was mechanically stirred for 2 hours in a water bath at 70° C., the magnetic microspheres were precipitated by a magnet, the liquid phase was removed, the magnetic microspheres were washed with 60 mL anhydrous ethanol each time for a total of 2 times, then the magnetic microspheres were washed with 60 mL distilled water each time for a total of 3 times to obtain magnetic microspheres A.

0.01 mol acrylic acid was moved into 100 mL solution X (an aqueous solution containing 2-morpholineethanesulfonic acid (MES, CAS: 4432-31-9) at a final concentration of 0.1 mol/L and NaCl at a final concentration of 0.5 mol/L)), 0.04 mol 1-(3-dimethylaminopropyl)-3-ethylcarbodiimide hydrochloride (EDC·HCl, CAS: 25952-53-8) and 0.04 mol N-hydroxysuccinimide (NHS, CAS: 6066-82-6) were added to the solution X, the obtained mixture was stirred at room temperature for 15 minutes, pH of the solution was adjusted to 7.2 with $NaHCO_3$ solid powder, the above-mentioned solution with pH adjusted was added to 100 mL PBS buffer solution containing 10 mL magnetic microspheres A and it was mechanically stirred for 20 hours in a water bath at 30° C., the magnetic microspheres were precipitated by a magnet, the liquid phase was removed, the magnetic microspheres were washed with 60 mL distilled water each time for a total of 6 times to obtain magnetic microspheres B.

12 mL 2.08 mol/L sodium acrylate solution was added to, and then 450 μL 10% (w/v) ammonium persulfate solution and 45 μL tetramethylethylenediamine were added to the solution, then the mixture was reacted at room temperature for 30 minutes, the magnetic microspheres were precipitated by a magnet, the liquid phase was removed, the magnetic microspheres were washed with 10 ml distilled water each time for a total of 6 times to obtain magnetic microspheres C.

Synthesized magnetic microsphere C was transferred to 10 mL solution X, 0.004 mol 1-(3-dimethylaminopropyl)-3-ethylcarbodiimide hydrochloride (EDC·HCl) and 0.004 mol N-hydroxysuccinimide (NHS) were added to the solution X, the mixture was stirred at room temperature for 30 minutes, the magnetic microspheres were precipitated by a magnet, the liquid phase was removed, then the magnetic microspheres were washed with 10 mL distilled water each time for a total of 3 times; 0.002 mol N,N-bis(carboxymethyl)-L-lysine (CAS: 113231 May 3) was weighed and dissolved in 10 mL solution Y, pH of the solution was adjusted to 7 with $NaHCO_3$ solid powder, and the solution was added to the cleaned magnetic microspheres, it was mechanically stirred in a water bath at 30° C. for 20 hours, 0.02 mol nickel sulfate solid particles were added to the reaction system and the solution was continually stirred for 2 hours, the magnetic microspheres were precipitated by a magnet, the liquid phase was removed, then the magnetic microspheres were washed with 6 mL distilled water each time for a total of 10 times to obtain magnetic microspheres D, a nickel magnetic beads, that is, the biomagnetic microsphere of the present invention, abbreviated as a KM magnetic bead hereinafter.

Example 2 Effect of Biomagnetic Microsphere

In order to verify the effect of KM magnetic beads, an experiment was carried out to compare the KM magnetic beads (the biomagnetic microsphere of the present invention, a nickel magnetic bead, and sodium acrylate was used as the monomer in the polymerization reaction) and control nickel beads. The control nickel beads were commercially available Sangon nickel beads (Ni-NTA agarose resin, catalog number: C600033-0025, Sangon Biotech (Shanghai), and an experiment was carried out to compare the KM magnetic beads and polyacrylic acid magnetic beads (prepared by our company's laboratory, acrylic acid was used as the monomer in the polymerization reaction), so as to implement an experiment to compare binding capacity and protein purity.

In this embodiment,

S20190820-1: the water phase replaced the Y solution, and TEMED was not used in the polymerization process (to promote polymerization).

S20190820-2: the magnetic microspheres B were prepared by KH570 modified route, polyacrylic acid magnetic beads (S20190820-2) were prepared by using acrylic acid as monomer molecules, TEMED was used and buffer solution was the Y solution.

Group A: the solutions X and Y were replaced by the water phase during the synthesis process. Acrylic acid was used as the polymerization monomer. Other preparation conditions were the same as those for the preparation of the KM magnetic beads in Example 1.

Group B: they were prepared with reference to the method of synthesis of the KM magnetic beads. Acrylic acid was used as the polymerization monomer. Other preparation conditions were the same as those for the preparation of the KM magnetic beads in Example 1.

2.1. Binding Capacity Comparison Test 2.1.1. Comparison of KM Magnetic Beads (Nickel Magnetic Beads) and Control Nickel Beads The KM magnetic beads were washed three times with binding buffer (50 mM Tris-HCl with pH 8.0, 500 mM sodium chloride, 5 mM imidazole), the supernatant and precipitate were separated. The control nickel beads were washed with the above binding buffer in the same manner, and then the supernatant and precipitate were separated. A corresponding amount of beads were placed in different centrifuge tubes according to Table 1 below.

TABLE 1

KM magnetic beads (nickel magnetic beads) and control nickel beads and their numbers

| No. | Amount of control nickel beads | No. | Amount of KM magnetic beads |
|---|---|---|---|
| S1 | 10 μL | M1 | 10 μL |
| S2 | 3.3 μL | M2 | 3.3 μL |
| S3 | 1.0 μL | M3 | 1.0 μL |

3 mL IVTT reaction solution expressing eGFP (with histidine tag attached to the N-terminal of eGFP) was acquired, 3 mL binding buffer (RFU value was 1265.33) was added to and they were mixed well, followed by centrifugation at 4000 rpm for 10 minutes at 4° C. The precipitate was discarded, 1 mL supernatant was added to each of the above-mentioned centrifuge tubes containing the bead suspension, then they were mixed thoroughly, and incubated at 4° C. for 3 hours under rotation.

The supernatant was separated to obtain flow-through solution. The beads were washed twice with 1 mL washing solution (50 mM Tris-HCl with pH 8.0, 500 mM sodium chloride, 20 mM imidazole), finally, the beads were eluted with 1 mL and 200 μL eluent (50 mM Tris-HCl with pH 8.0, 500 mM sodium chloride, 250 mM imidazole), respectively. For each step of washing or elution, all of them were incubated at 4° C. for 5 to 10 minutes under rotation, the supernatant obtained at each step was collected, the RFU value was measured by using a Tecan Infinite F200/M200 multifunctional microplate reader, and the product content was calculated.

According to the purified eGFP, a standard curve was drawn up, and a conversion formula between the protein mass concentration of eGFP and its corresponding RFU value was calculated, and the conversion formula obtained was as follows:

$$X = -\frac{1}{0.0005} \times \ln\left(1 - \frac{Y - 38.089}{31692}\right).$$

Wherein, X represented the protein mass concentration (μg/mL), and Y was the RFU fluorescence reading.

The binding capacity of magnetic microsphere was calculated as follows: the value of Y was substituted into the above formula to obtain the value of X. Wherein, the obtained X was the protein mass concentration. X was multiplied by the elution volume to obtain the eluted protein mass (W). W was divided by the column bed volume of the magnetic microsphere (for example, the volume of column bed No. S1 was 10 μL) to obtain the mass of the target protein binding to the magnetic microsphere per unit volume, and the obtained mass was the binding capacity in mg/mL.

The results show that the binding capacity of the KM magnetic beads is more than 3 times higher than that of the control nickel beads (see Table 2).

TABLE 2

Comparison of binding capacity between KM magnetic beads and control nickel beads

| | 10 μL | | 3.3 μL | | 1.0 μL | |
|---|---|---|---|---|---|---|
| RFU value | KM magnetic bead | Control nickel bead | KM magnetic bead | Control nickel bead | KM magnetic bead | Control nickel bead |
| IVTT reaction solution | | | 1265.33 | | | |
| Flow-through solution | 29.33 | 80.67 | 38.33 | 582.00 | 678.67 | 1083.67 |
| Washing solution 1 | 12.67 | 148.00 | 48.00 | 195.00 | 208.67 | 98.33 |
| Washing solution 2 | 10.33 | 98.00 | 64.33 | 63.33 | 130.67 | 26.00 |
| Eluent 1 | 1477.33 | 810.67 | 1328.67 | 406.00 | 551.33 | 59.00 |
| Eluent 2 | 228.00 | 75.00 | 144.33 | 40.33 | 31.00 | 8.67 |
| Binding capacity (mg/mL) | 10 | 4 | 28 | 8 | 32 | 2 |

2.1.2. Comparison of Binding Capacity Between KM Magnetic Beads and Polyacrylic Acid Magnetic Beads (S20190820-1 Magnetic Beads)

The KM magnetic beads were prepared by the method of Example 1, and sodium acrylate was used as the monomer for polymerization.

Acrylic acid, instead of sodium acrylate, was used as the monomer for polymerization to prepare polyacrylic acid magnetic beads (S20190820-1). The solution Y was replaced by an aqueous phase during the synthesis.

IVTT reaction solution with the same volume and the same source was treated, respectively. Comparison of binding capacity was made by using the test analysis method shown in 2.2.1, and results were shown in Table 3. Both the IVTT reaction solution and the flow-through solution had a volume of 1 mL (the flow-through liquid loss can be negligible). The results showed that RFU value of the flow-through liquid of the KM magnetic beads was only 272, and RFU value of the flow-through liquid of polyacrylic acid magnetic beads (S20190820-1 magnetic beads) was significantly higher than 272 and was even reached 1188 when the column bed volume was 2 μL, wherein the value was 4-5 times that of the KM magnetic beads. The results showed that the binding capacity of the KM magnetic beads was more than 20 times that of the polyacrylic acid magnetic beads (S20190820-1) when the column bed volume was 2 μL, and it was about 21 times, 26 times that of the polyacrylic acid magnetic beads (S20190820-1) when the column bed volume was 10 μL and 50 μL. As a result, in order to achieve the same effect of the KM magnetic beads, the amount of the polyacrylic acid magnetic beads should be at least 20 times that of the KM magnetic beads.

TABLE 3

Comparison of binding capacity between KM magnetic beads and S20190820-1 magnetic beads

| RFU value | 2 μL column bed | | 10 μL column bed | 50 μL column bed |
|---|---|---|---|---|
| | KM magnetic bead | S20190820-1 | S20190820-1 | S20190820-1 |
| Flow-through solution | 272 | 1188 | 866 | 311 |

2.1.3. Analysis of Effect of Polyacrylic Acid Magnetic Beads

Polyacrylic acid magnetic beads were prepared by using acrylic acid as the polymerization monomer instead of sodium acrylate.

The KM magnetic beads were prepared by the method of Example 1.

Polyacrylic acid magnetic beads were prepared under the following two different conditions.

Group A: the solutions X and Y were replaced by the water phase during the synthesis process. Acrylic acid was used as the polymerization monomer. Other preparation conditions are the same as those for the preparation of the KM magnetic beads in Example 1.

Group B: they were prepared with reference to the synthesis method of the KM magnetic beads. Acrylic acid was used as the polymerization monomer. Other preparation conditions are the same as those for the preparation of the KM magnetic beads in Example 1.

Figure 2:
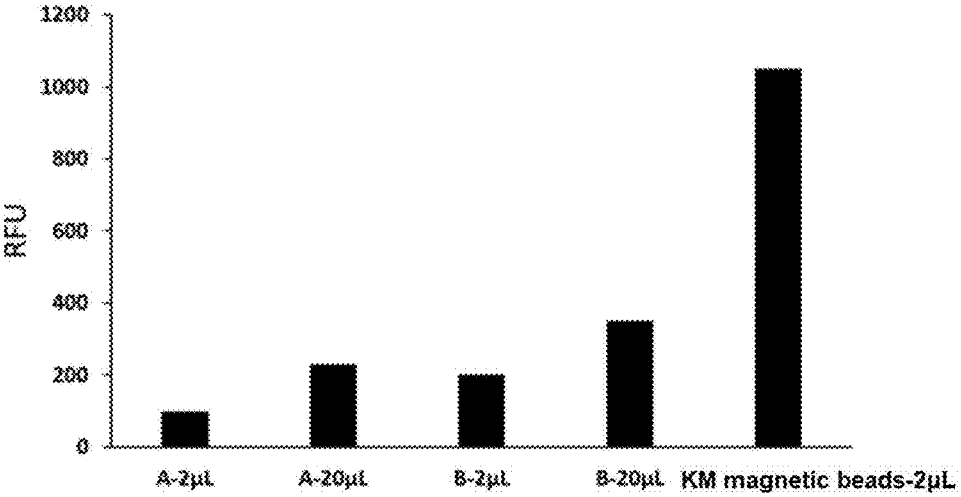
FIG. 2 shows a comparison of the difference of RFU value of IVTT reaction solution before and after the treatment by polyacrylic acid magnetic beads and the KM magnetic beads (the difference is obtained by RFU value of the IVTT reaction solution minus RFU value of the flow-through solution). Groups A and B correspond to two kinds of polyacrylic acid magnetic beads synthesized under different conditions. Group B is prepared according to the synthesis method of the KM magnetic beads. During the process of synthesis of group A, solution X and solution Y are replaced with a water phase. The volume (2 μL, 20 μL) in the label on the abscissa corresponds to the amount of magnetic beads, representing 2 μL magnetic beads and 20 μL magnetic beads, respectively.

Referring to the test analysis method in section 2.1.1, each group was treated with IVTT reaction solution with the same volume and the same source. FIG. 2 showed a comparison of a difference of RFU value of polyacrylic acid magnetic beads prepared in Group A and Group B and the KM magnetic beads before and after the treatment of IVTT reaction solution, that is, the difference is obtained by RFU value of the IVTT reaction solution minus RFU value of the flow-through solution. The analysis results showed that the binding capacity of the KM magnetic beads was much higher than that of the polyacrylic acid magnetic beads. In particular, the binding capacity of the KM magnetic beads may be 5-10 times that of the polyacrylic acid magnetic beads; when the column bed volume was 2 μL, the binding capacity of the KM magnetic beads was 10 times, 5 times that of the polyacrylic acid magnetic beads prepared in Group A and Group B, respectively.

2.1.4. KH570 Modified Route

For KH550 modified route, amino groups were first introduced by using an aminated silane coupling agent KH1550 (3-aminopropyltriethoxysilane, CAS: 919-30-2) (to obtain a magnetic microsphere A), then carbon-carbon double bonds were introduced to obtain a magnetic microsphere B.

The KH570 modified route was different from the KH550 modified route. The KH570 modified route adopted trimethoxysilanized methacrylic acid molecule KH570 (CAS: 2530-85-0, 3-(methacryloxy)propyltrimethoxysilane, an allyl silane coupling agent) to modify the magnetic microsphere body, and directly introduced the carbon-carbon double bonds to obtain the magnetic microsphere B.

Figure 3:
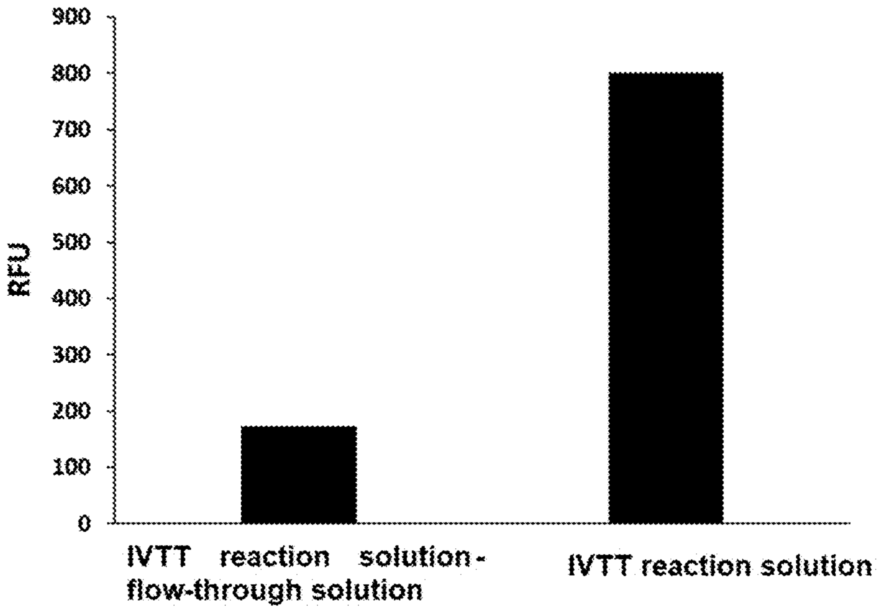
FIG. 3 shows a comparison of the RFU value (obtained by RFU value of the IVTT reaction solution minus RFU value of the flow-through solution) of the polyacrylic acid magnetic beads prepared by the KH570 modification route and the RFU value of the IVTT reaction solution.

The KH570 modified route was used to prepare the magnetic microspheres B, and acrylic acid was used as the monomer molecule to prepare and obtain the polyacrylic acid magnetic beads (S20190820-2), and the buffer was Y solution. The IVTT reaction solution with the same volume and the same source was treated, respectively, and the method in 2.1.1. was used for test and analysis. The volume of the magnetic beads used was 20 μL, and the volume of IVTT reaction solution was 1 mL. The RFU values of the IVTT reaction solution (original solution), the flow-through solution, the washing solution, and the eluent were tested respectively. The RFU value of the IVTT reaction solution was 800 and the RFU value of the flow-through solution was 173. The results were shown in FIG. 3. The analysis results showed that the binding capacity (about 2 mg/mL) of the polyacrylic acid magnetic beads obtained by the KH570 modified route was lower than that of the above-mentioned KM magnetic beads.

2.1.5. Preparation of B-KM Magnetic Beads Using Polymerization Monomers with Different Concentration Compared with the preparation method of the KM magnetic beads, the monomer concentration of the polymerization monomer, sodium acrylate, was increased from 2.08 mol/L to 2.496 mol/L. The other preparation methods and parameters were the same as those in Example 1, and sodium polyacrylate magnetic beads (B-KM magnetic beads, 191220-ZZ-1) were obtained.

The binding capacity was tested and analyzed by using the method in 2.1.1., and the result was shown in Table 4. Magnetic beads with different volumes (2 μL, 4 μL, 8 μL) were used to carry out three tests of the binding capacity. It was found that the magnetic beads were excessive when the volume of the magnetic beads was 4 μL and 8 μL. The binding capacity of the magnetic beads with a volume of 2 μL was calculated to be about 85.6 mg/mL by the above-mentioned formula in 2.1.1.

TABLE 4

| Test and analysis of binding capacity of B-KM magnetic beads (191220-ZZ-1) | | | | | | |
|---|---|---|---|---|---|---|
| Amount of beads | RFU value | | | | Binding efficiency | Binding capacity |
| magnetic | Total | Flow-through | E1 | E2 | (%) | (mg/ml) |
| 2 μL | 4428 | 214 | 20241 | 1729 | 95.2 | 85.6 |
| 4 μL | | 132 | 23862 | 2741 | 97.0 | / |
| 8 μL | | 93 | 23675 | 5631 | 97.9 | / |

In Table 4, Total corresponds to IVTT reaction solution to be treated, Flow-through corresponds to the flow-through solution, E1 corresponds to solution obtained by the first elution process with 80 μL eluent, and E2 corresponds to solution obtained by the second elution process with 80 μL eluent.

2.2. Purity Test 2.2.1. Purity Test of Purified Products of KM Magnetic Beads and Control Nickel Beads

TABLE 5

| Purity test: | | | |
|---|---|---|---|
| No. | IVTT reaction solution expressing eGFP (it is reacted after addition of DNA template) | IVTT reaction solution not expressing eGFP (it is reacted without addition of DNA template) | Concentration of IVTT reaction solution diluted |
| 1 | 1 mL | 0 | 100% |
| 2 | 0.8 mL | 0.2 mL | 80% |
| 3 | 0.6 mL | 0.4 mL | 60% |
| 4 | 0.4 mL | 0.6 mL | 40% |
| 5 | 0.2 mL | 0.8 mL | 20% |
| 6 | 0.1 mL | 0.9 mL | 10% |
| 7 | 0.01 mL | 0.99 mL | 1% |
| 8 | 0 mL | 1 mL | 0% |

The control nickel beads and the KM magnetic beads in section 2.1.1. were washed three times with binding buffer (50 mM Tris-HCl with pH 8.0, 500 mM sodium chloride, 5 mM imidazole), respectively, the supernatant and precipitate were separated. 3 μL of each kind of beads was pipetted into 8 centrifuge tubes (as shown in Table 5), respectively.

6 mL of the IVTT reaction solution expressing eGFP and 6 mL of the IVTT reaction solution not expressing eGFP were acquired, and the acquired IVTT reaction solutions was centrifuged separately at 4000 rpm, at 4° C. for 10 minutes, respectively. The precipitate was discarded, the supernatants of the two kinds of IVTT reaction solution were mixed at a ratio by volume in Table 5 to obtain 8 groups of solution with different eGFP protein concentration. The 8 groups of solution were added to corresponding bead centrifuge tubes, respectively (the KM magnetic beads and the control nickel beads were used, respectively) and they were mixed thoroughly and were incubated at 4° C. for 1.5 hours under rotation.

The IVTT reaction solution expressing eGFP refers to a reaction solution obtained by using an IVTT system (using a DNA template encoding eGFP) to perform in vitro protein synthesis reaction. The IVTT reaction solution not expressing eGFP, as a diluent, means that a DNA template encoding eGFP was not added to the IVTT system, and proteins in the reaction solution thus obtained were all impure proteins. If the reaction solution not expressing target proteins were mixed into the IVTT reaction solution, different proportion of impure proteins may be incorporated into the IVTT reaction. SDS-PAGE electrophoresis was performed on solution with different eGFP protein concentration, and the purity of the purified eGFP proteins was compared. In Table 5, the lower the concentration of the diluted IVTT reaction solution, the lower the content of the target proteins, and the more the content of the impure proteins.

The supernatant was separated to obtain flow-through solution. The control nickel beads and the KM magnetic beads were washed twice with 1 mL washing solution (50 mM Tris-HCl with pH 8.0, 500 mM sodium chloride, 20 mM imidazole), respectively; finally, the beads were eluted with 200 μL eluent (50 mM Tris-HCl with pH 8.0, 500 mM sodium chloride, 250 mM imidazole) only once. For each step of washing or elution, all of them were incubated at 4° C. for 5 to 10 minutes under rotation, the supernatant obtained at each step was collected, the RFU value was measured.

30 μL of the eluate was added to 8 μL loading buffer (250 mM Tris-HCl with pH 6.8, 10% (w/v) SDS, 0.5% (w/v) bromophenol blue (BPB, CAS: 115-39-9), 50% (v/v) glycerol, 5% (v/v) (3-mercaptoethanol), and the resulting mixture was boiled evenly for 8 minutes, and SDS-PAGE electrophoresis detection was performed on all the loading samples. Results were shown in FIG. 1. The gel image in FIG. 1 was analyzed with Image-J software to obtain the brightness values of bands. The calculation results were shown in Table 6.

In table 6, lane was the number of each lane, Total was the total brightness of each band in each lane, and eGFP was the brightness of a target band (eGFP, about 26.7 kDa) in each lane. eGFP/Total reflects the content ratio of the target proteins in the sample obtained from purification of the magnetic beads.

A ratio of the brightness of the target band eGFP to the total brightness of each band, i.e., eGFP/Total, represented purity. The results showed that the purity obtained by the purification of the KM magnetic beads was better than that obtained by the purification of the control nickel beads. Wherein, the purity of purified products of the KM magnetic beads can be up to 92.5%.

TABLE 6

| Comparison of the brightness value of the electrophoretic detection bands of the samples obtained by purification of the two magnetic beads | | | | |
|---|---|---|---|---|
| Magnetic beads used | lane | eGFP | Total | eGFP/Total |
| KM magnetic beads | 1 | 10061.5 | 11094 | 0.907 |
| | 2 | 9882.4 | 11001.4 | 0.898 |
| | 3 | 9684.8 | 10466.8 | 0.925 |
| | 4 | 9139.4 | 9959.5 | 0.918 |
| | 5 | 8121.6 | 9480.6 | 0.857 |
| | 6 | 6433.6 | 8999 | 0.715 |
| | 7 | 6057 | 35508.4 | 0.171 |
| | 8 | 2536.1 | 72200.9 | 0.035 |
| Control nickel beads | 1 | 8164.4 | 9441.8 | 0.865 |
| | 2 | 8008.2 | 9237.6 | 0.867 |
| | 3 | 7509.4 | 8649.6 | 0.868 |
| | 4 | 7006.6 | 8061.7 | 0.869 |
| | 5 | 5847.6 | 6592.9 | 0.887 |
| | 6 | 5025.7 | 6278.2 | 0.801 |
| | 7 | 4221.3 | 37958.9 | 0.111 |
| | 8 | 1765 | 56558.8 | 0.031 |

2.2.2. Purity Test of Purified Products of B-KM Magnetic Beads

Figure 4:
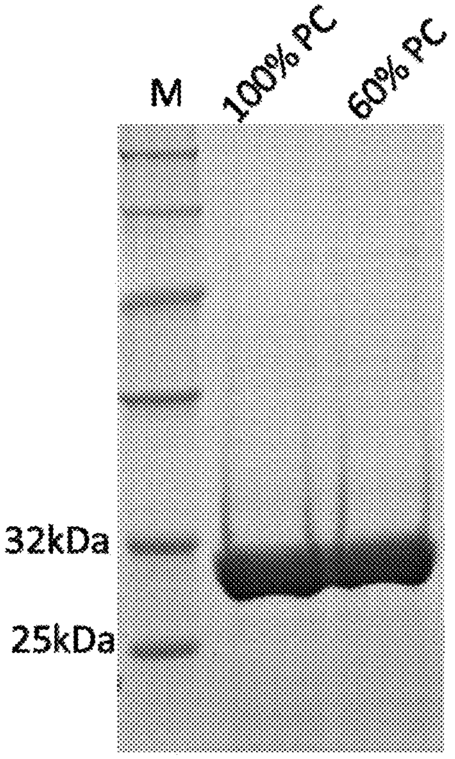
FIG. 4 shows an electrophoresis diagram of the purity test of sodium polyacrylate magnetic beads (B-KM magnetic beads, 191220-ZZ-1), where 100% refers to pure IVTT reaction solution without dilution; 60% refers to 60% (by volume) of the pure IVTT reaction solution being mixed with 40% (by volume) of diluent.

Purity test and analysis of the B-KM magnetic beads obtained in the above-mentioned section 2.1.5. were performed. The brightness value of each band in the electrophoresis spectrogram was analyzed with Image-J software. Results showed that the purity of the target proteins can be up to 97%. Referring to FIG. 4, 100% refers to the pure IVTT reaction solution; 60% refers to the mixing of 60% of the pure IVTT reaction solution by volume and 40% of diluent by volume.

Example 3 Verification of the Effect of Biomagnetic Microsphere 3.1. Isolation and Purification of Firefly Luciferase In order to further verify the effect of the KM magnetic beads, the IVTT reaction was carried out to express firefly luciferase (which can be abbreviated as luciferase), and affinity analysis was performed. The firefly luciferase contains a histidine tag, and the obtained protein product is a label of the His tag.

The KM magnetic beads and the control nickel beads were washed three times with binding buffer (50 mM Tris-HCl with pH 8.0, 500 mM sodium chloride, 5 mM imidazole), the supernatant and precipitate were separated. 3 μL of each kind of beads was pipetted into 7 centrifuge tubes (as shown in Table 7).

1 mL of the IVTT reaction solution expressing firefly luciferase (containing a histidine tag) was acquired, and the acquired IVTT reaction solution was centrifuged at 4000 rpm, at 4° C. for 10 minutes. The precipitate was discarded, the supernatant was mixed with the binding buffer at a ratio by volume in Table 7. The resulting mixture was added to corresponding centrifuge tubes, and they were mixed thoroughly and incubated at 4° C. for 1 hour under rotation.

TABLE 7

| IVTT firefly luciferase system | | | |
|---|---|---|---|
| | Luciferase | Amount of samples added to 1 mL system | |
| No. | percentage/% | Luciferase/μL | Binding buffer/μL |
| 1 | 5 | 50 | 950 |
| 2 | 2 | 20 | 980 |
| 3 | 1.5 | 15 | 985 |
| 4 | 1 | 10 | 990 |
| 5 | 0.8 | 8 | 992 |
| 6 | 0.6 | 66 | 994 |
| 7 | 0.4 | 4 | 996 |

The supernatant was separated to obtain flow-through solution. The beads were washed twice with 1 mL w ashing solution (50 mM Tris-HCl with pH 8.0, 500 mM sodium chloride, 20 mM imidazole); finally, the beads were eluted with 200 μL eluent (50 mM Tris-HCl with pH 8.0, 500 mM sodium chloride, 250 mM imidazole) only once. For each step of washing or elution, all of them were incubated at 4° C. for 5 to 10 minutes under rotation, the supernatant obtained at each step was collected, the RFU value was measured by using a Tecan Infinite F200/M200 multifunctional microplate reader.

TABLE 8

| Detection results of firefly luciferase treated with IVTT reaction solution | | | | | |
|---|---|---|---|---|---|
| No. | Luciferase percentage (%) | Reaction solution RLU value | Flow-through solution RLU value | Binding efficiency (%) | Substrate concentration (mg/mL) |
| 1 | 5 | 168497750 | 6832107 | 95.9 | 0.339 |
| 2 | 2 | 63708857 | 2866446 | 95.5 | 0.129 |
| 3 | 1.5 | 51453687 | 2366899 | 95.4 | 0.105 |
| 4 | 1 | 23863700 | 1249596 | 94.8 | 0.049 |
| 5 | 0.8 | 15474300 | 847806 | 94.5 | 0.033 |
| 6 | 0.6 | 10211157 | 623941 | 93.9 | 0.022 |
| 7 | 0.4 | 6620700 | 406262 | 93.9 | 0.015 |

According to the following formula: binding efficiency=(1-flow-through solution RLU value/reaction solution RLU value)×100%, the binding efficiency was calculated, and the value of the affinity was the concentration of the substrate when 50% of the substrate was bound.

According to the purified luciferase, a standard curve was drawn up, and the formula to convert the RLU value of luciferase into protein mass concentration was inferred as: Y=5(E+08)X−850502, that is, $Y=5\times10^8\times X-850502$. Wherein, X represented the protein mass concentration (μg/mL), and Y was the RFU fluorescence reading. In the test range, Y was basically proportional to X.

The measured RLU readings of the reaction solution and the flow-through solution were substituted into the above formula to calculate the target protein concentration, respectively.

It can be seen from the experimental results (Table 8) that when the mass concentration of the target protein is reduced from 339 μg/ml to 15 μg/ml, the binding efficiency of the KM magnetic beads to the target proteins is still much higher than 90%. Since the RLU value of the reaction solution in No. 7 is close to the detection limit of the instrument, so the target protein concentration is not further reduced to reduce the binding efficiency to 50%, so as to obtain the specific value of the affinity. But a semi-qualitative conclusion can be obtained, that is, the KM magnetic bead has a strong affinity to the target protein, and its affinity can reach at least the ng/ml level.

3.2. Affinity Test and Analysis of B-KM Magnetic Beads

Sodium polyacrylate magnetic beads (200224-ZZ-1) were prepared using the method for preparing B-KM magnetic beads in above mentioned section 2.1.5. Affinity test and analysis were carried out by using the IVTT reaction solution expressing eGFP according to the method described in section 3.1., and results were shown in Table 9. The binding efficiency was greater than 90% and can be up to 99.3%.

When the concentration, at which 90% target proteins were adsorbed (90% binding efficiency), was 0.3 μg/mL (300 ng/mL), a semi-qualitative conclusion can be obtained, that is, the affinity of the magnetic beads can reach the ng/mL level.

TABLE 9

Affinity analysis of B-KM magnetic beads

| eGFP percentage (%) | RFU value Reaction solution Total | Flow-through solution (200224-ZZ-1) | NC | Binding efficiency (%) (200224-ZZ-1) |
|---|---|---|---|---|
| 0 | 1 | 1 | 2 | 0.0 |
| 0.5 | 32 | 2 | 1 | 96.8% |
| 1 | 58 | 3 | 2 | 98.2% |
| 2 | 127 | 7 | 5 | 98.4% |
| 5 | 310 | 8 | 6 | 99.3% |
| 10 | 556 | 11 | 7 | 99.3% |

Wherein, NC is a negative control, and its RFU value is used as background value.

The calculation formula of the binding efficiency is: (reaction solution RFU value−flow-through solution RFU value)/(reaction solution RFU value−NC RFU value).

Example 4 Effect Investigation of the Size of Magnetic Microspheres on the Purification Effect 4.1. Preparation of $SiO_2$-Coated Magnetic Microspheres (Also Referred to Magnetic Microsphere Body, Magnetic Beads, Glass Beads)

20 g $Fe_3O_4$ microspheres were put into a mixed solvent of 310 mL ethanol and 125 mL water, 45 mL 28% (wt) ammonia water was added into the mixture, and 22.5 mL tetraethyl orthosilicate was added dropwise, then the mixture was stirred and reacted at room temperature for 24 hours. After the reaction was completed, the microspheres were washed with ethanol and water. $Fe_3O_4$ microspheres with different particle sizes (about 1 μm, 10 μm, 100 μm) were used as raw materials, and the particle sizes of the obtained glass beads were controlled. The $Fe_3O_4$ microspheres with different particle sizes can be prepared by conventional technical means.

The prepared magnetic microspheres are used as a basic material for modifying purification media or for connecting elements-purification media, so they are also referred to magnetic microsphere body.

The prepared magnetic microspheres have a magnetic core, which can be controlled by magnetic force to achieve movement, dispersion, sedimentation and other operations, so they are a kind of magnetic beads in a broad sense.

The prepared magnetic microspheres have a $SiO_2$-coated layer, so they are also referred to glass beads, which can reduce the adsorption of the following compositions or components by the magnetic core: polymers, purification media, components of the in vitro protein synthesis system, nucleic acids templates, protein expression products, and the like.

4.2. Preparation of Nickel Magnetic Beads with Different Sizes of Glass Beads ($SiO_2$-Coated Magnetic Microspheres)

Glass beads with diameters of 1 μm, 10 μm, and 100 μm were prepared as magnetic microsphere bodies by the preparation method shown in step 4.1., then nickel magnetic beads Ni1, Ni10, and Ni100 were prepared by using the method of Example 1, respectively. Other reaction parameters were all the same except for the raw materials for the glass beads.

Figure 5:
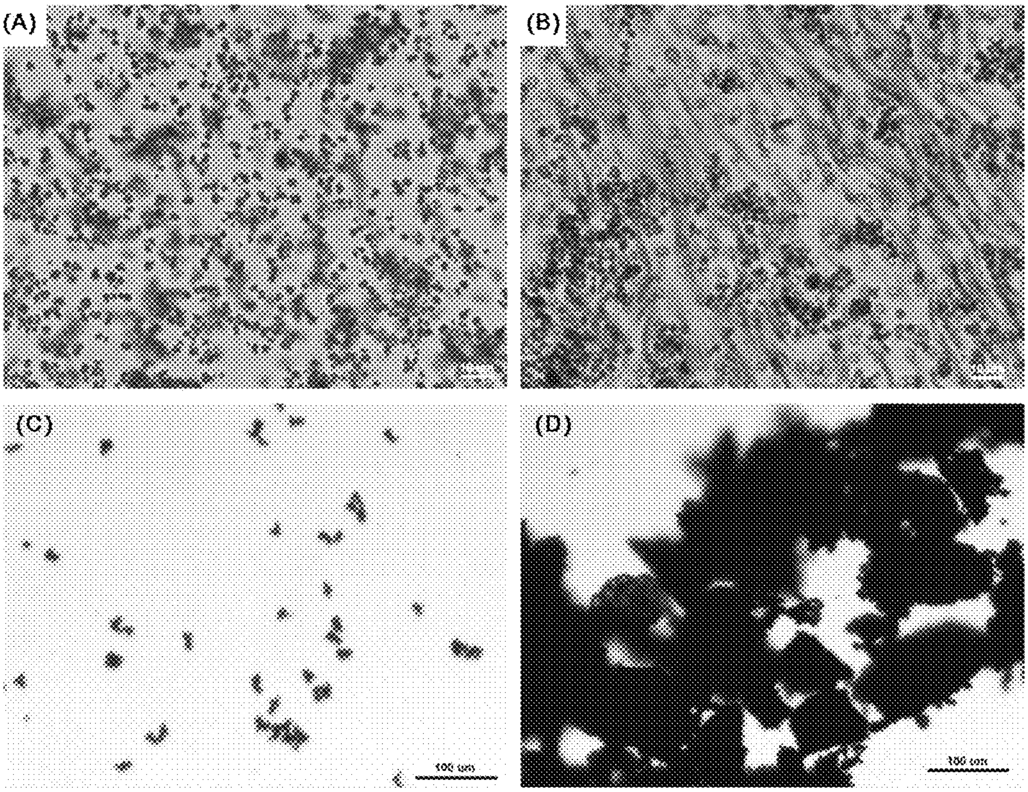
FIG. 5 shows an inverted microscope photograph of a $SiO_2$-coated magnetic microsphere body. (A) Diameter 1 μm, in a static state; (B) Diameter 1 μm, in a flowing state; (C) Diameter 10 μm; (D) Diameter 100 μm. Each scale of Figures (A) and (B) is 10 μm; each scale of Figures (C) and (D) is 100 μm.

Take pictures with a microscope to observe the size and morphology of the prepared nickel magnetic beads. The results were shown in FIG. 5, and glass beads with diameters of about 1 μm (FIGS. 5 (A) and (B)), 10 μm (FIG. 5 (C)), and 100 μm (FIG. 5 (D)) were obtained. FIG. 5(A) is a picture taken in a static state, and FIG. 5(B) is a picture taken in a flowing state.

4.3. Comparison of Results of Purification of IVTT Reaction Solution 4.3.1. Construction of In Vitro Protein Synthesis System (D2P System, DNA-to-Protein System)

In vitro protein synthesis reaction was carried out in a flat-bottomed cell culture plate. 3 parallel samples were set for each sample, and the mean and standard deviation (error bar) were calculated.

The final concentrations of respective component are: 9.78 mM Tris·HCl with pH 8.0, 80 mM potassium acetate, 5 mM magnesium acetate, 1.8 mM nucleoside triphosphate mixture (including adenosine triphosphate, guanosine triphosphate, cytidine triphosphate, and uridine triphosphate, the concentration of each type of nucleoside triphosphate is 1.8 mM), 0.7 mM amino acid mixture (including glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine, and histidine, the concentration of each type of amino acid is 0.1 mM), 15 mM glucose, 320 mM maltodextrin (the molar concentration is calculated in glucose units, and the mass volume concentration is 52 mg/mL), 24 mM tripotassium phosphate, 2% (w/v) polyethylene glycol 8000, and finally 50% by volume of *Kluyveromyces lactis* cell extract; the *Kluyveromyces lactis* cell extract contains endogenously expressed T7 RNA polymerase.

The *Kluyveromyces lactis* cell extract was prepared by using the method recorded in CN109423496A. Generally, the coding gene of the T7 RNA polymerase was integrated into the genome of *Kluyveromyces lactis*, and the obtained genetically modified strain was used for culturing; after an appropriate amount of cells were obtained, the cell extract was prepared.

4.3.2. Preparation of Nucleic Acid Template (DNA Template) Encoding 8His-mEGFP

The DNA fragment containing the coding gene of 8His-mEGFP (mEGFP labeled with histidine tag, wherein mEGFP is an A206K mutant of eGFP) was inserted into the plasmid vector to construct a plasmid vector expressing mEGFP by using PCR amplification and homologous fragment recombination method. The plasmid was confirmed to be correct by gene sequencing. The plasmid vector comprised the following components: T7 promoter, 5'UTR, coding sequence of leader peptide, 8×His (histidine tag), mEGFP coding sequence, 3'UTR, LAC4 terminator, fl ori (replication origin site), AmpR promoter, AmpR gene (ampicillin resistance gene), ori (high copy number replication origin site), lacI promoter, lad (lac inhibitor) coding gene and other functional elements.

By adopting RCA amplification method, the plasmid DNA encoding 8His-mEGFP was used as a nucleic acid template, and the phi29 DNA polymerase was used to perform in vitro DNA amplification to obtain the DNA template encoding 8His-mEGFP.

4.3.3. Performing In Vitro Protein Synthesis Reaction (IVTT Reaction)

The DNA template encoding 8His-mEGFP (15 ng/uL) prepared in 4.3.2. was added to the in vitro protein synthesis system constructed in 4.3.1., and they were mixed well. The mixture was reacted with shaking at room temperature (20~30° C.) for 3 hours. After the reaction was completed, the IVTT reaction solution (PC group, original protein solution) was obtained.

4.4. Purification and RFU Test

The IVTT reaction solution was purified with nickel magnetic beads with different sizes prepared in 4.2., and the influence of the size of the magnetic microsphere body on the purification effect was investigated.

1 mL IVTT reaction solution was pipetted, and 10 μL, 5 μL, 1 μL nickel magnetic beads Ni1 (1 μm), 10 μL, 5 μL, 1 μL nickel magnetic beads Ni10 (10 μm), 10 μL, 5 μL, 1 μL nickel magnetic beads Ni100 (100 μm) were added to the 1 mL IVTT reaction solution. The solution was rotated with a rotator to mix well, and it was incubated for 3 hours. A magnet was used to separate the magnetic beads from the solution, and the collected supernatant was recorded as the penetrating solution. Fluorescence test was performed on the penetrating solution, and the RFU value reflects the amount of protein not bound to the magnetic beads. Sample treatment: the sample was centrifuged at 4000 rpm, at 4° C. for 1 minutes. The sample to be tested was placed in the microplate reader, excitation wavelength/emission wavelength (Ex/Em): 488 nm/507 nm507 nm, was used to determine the relative fluorescence unit (RFU).

4.5. Analysis of Purification Results

Figure 6:
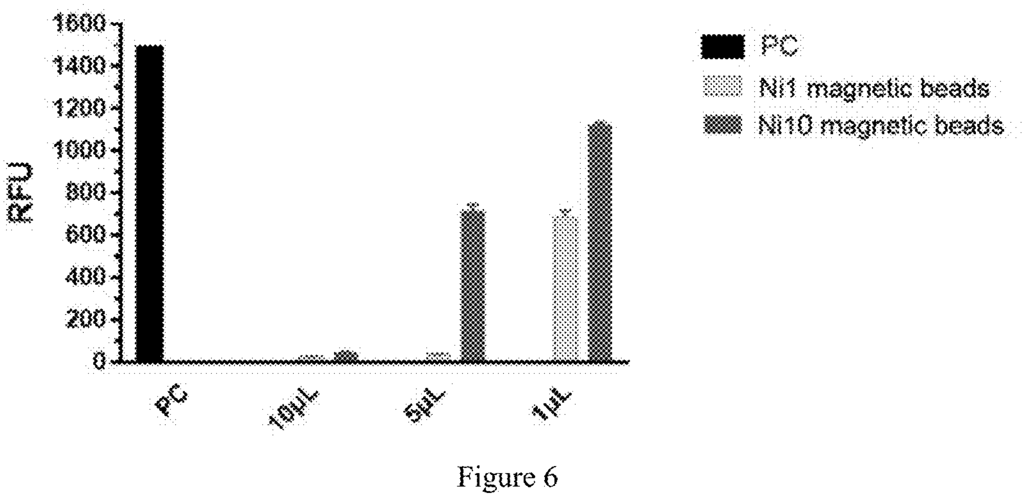
FIG. 6 shows a comparison of the purification effect of KM magnetic beads (nickel magnetic beads) prepared with 1 μm and 10 μm magnetic microspheres. Wherein, PC corresponds to primary solution (IVTT reaction solution, 1 mL reaction system) to be purified; Ni1 magnetic beads and Ni10 magnetic beads use 1 μm and 10 μm magnetic microsphere bodies, respectively; 10 μL, 5 μL and 1 μL correspond to the volume of the nickel magnetic beads used, respectively.

The comparison of the purification results of nickel magnetic beads Ni1 (1 μm) and nickel magnetic beads Ni10 (10 μm) was shown in FIG. 6. The comparison of the purification results of nickel magnetic beads Ni1 (1 μm) and nickel magnetic beads Ni10 (100 μm) was shown in FIG. 7. Wherein, the PC group was the RFU test result of the IVTT reaction solution obtained in 4.3.3. 10 μL, 5 μL, and 1 μL represented the volume of the nickel magnetic beads added, respectively. The RFU value of the PC group was subtracted by the RFU value of the penetrating solution to obtain a difference, wherein the difference corresponded to the amount of protein bound in the magnetic beads, then protein binding efficiency can be estimated.

In FIG. 6, the concentration of the protein product 8His-mEGFP in the IVTT reaction solution was 97.4 μg/mL. Protein binding efficiency of the nickel magnetic beads Ni1 (1 μm) was 98.2%, 97.6%, and 53.8%, respectively when the amount by volume of the nickel magnetic beads Ni1 (1 μm) were 10 μL, 5 μL, and 1 μL. Protein binding efficiency of the nickel magnetic beads Ni10 (10 μm) was 96.9%, 51.9%, and 24.7%, respectively when the amount by volume of the nickel magnetic beads Ni10 (10 μm) were 10 μL, 5 μL, and 1 μL. The protein binding efficiency of nickel magnetic beads Ni1 (1 μm) was increased by 1.3%, 46.8%, and 54.1%, respectively.

Figure 7:
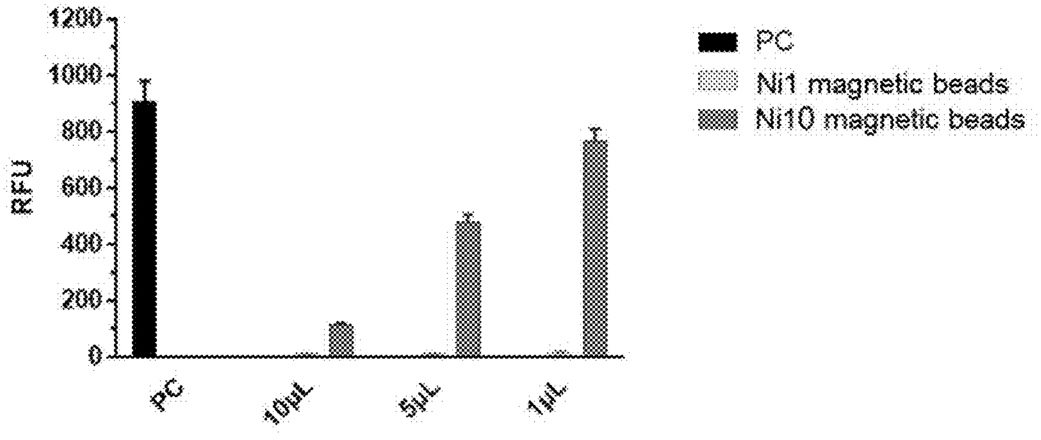
FIG. 7 shows a comparison of the purification effect of KM magnetic beads (nickel magnetic beads) prepared with 1 μm and 100 μm magnetic microspheres. Wherein, PC corresponds to primary solution (IVTT reaction solution, 1 mL reaction system) to be purified; Ni1 magnetic beads and Ni100 magnetic beads use 1 μm and 100 μm magnetic microsphere bodies, respectively; 10 μL, 5 μL and 1 μL correspond to the volume of the nickel magnetic beads used, respectively.

In FIG. 7, the concentration of the protein product 8His-mEGFP in the IVTT reaction solution was 57.9 μg/mL. The protein binding efficiency of the nickel magnetic beads Ni1 (1 μm) with three different volumes was all higher than 98% (98.3%-98.9%); protein binding efficiency of the nickel magnetic beads Ni100 (100 μm) was 87.5%, 46.9%, and 15.2%, respectively when the amount by volume of the nickel magnetic beads Ni1 100 (100 μm) were 10 μL, 5 μL, and 1 μL. The protein binding efficiency of nickel magnetic beads Ni1 (1 μm) was increased by 11.5%, 52.5%, and 84.6%, respectively.

Example 5 Investigation of the Influence of Polymer Chain Length 5.1. Preparation of Magnetic Microspheres with Different Polymer Chain Lengths Magnetic microspheres were prepared with nickel ions as the purification medium by using the method of Example 1, wherein the concentration of the polymerized monomer sodium acrylate was 2.08 mol/L and 2.496 mol/L, respectively, denoted as L15 and L18.

5.2. Purification and RFU Test

PC solution (IVTT reaction solution obtained when the IVTT reaction was completed) was prepared by the method described in 4.3. in Example 4. The PC solution was diluted at different ratios to obtain the original protein solution containing protein product (8His-mEGFP) with different concentration.

A negative control (NC group) was set: referring to the PC group, same operations were performed without addition of DNA template and the obtained "IVTT reaction solution" was the NC group.

Purification was carried out using the method of 4.4. in Example 4. 1 mL of the original protein solution with different dilution ratios was obtained, 2 μL nickel magnetic beads were added and they were incubated for reaction. Penetrating solution from which the magnetic beads were separated and two sets of eluents (eluent 1, eluent 2), were collected, respectively.

The RFU test was carried out using the method in 4.4. in Example 4 (Table 10 and Table 11). SDS-PAGE electrophoresis test was also performed (figure was not shown). SDS-PAGE electrophoresis was performed on the solution to be tested. Coomassie Brilliant Blue R-250 was used for dyeing, and it was left overnight. After decolorization, the target protein bands were observed, which can be used to analyze whether the molecular weight of the target protein was correct and to analyze the purity of the target protein. Detect parameters: 30 μL of the elution solution containing the fusion protein product was obtained, 7.5 μL of 5×loading buffer containing 5% B-mercaptoethanol was added to the elution solution, then the mixture was heated at 95° C. for 10 minutes, and SDS-PAGE electrophoresis was performed. Coomassie Brilliant Blue R-250 was used for dyeing, and it was left overnight. After decolorization, sizes of the target protein bands and the purity thereof were observed.

In Table 10, the protein binding efficiency was calculated by the following formula $1-(RFU_{ft}-RFU_0)/(RFU_{ori}-RFU_0)$, that is, $(RFU_{ori}-RFU_{ft})/(RFU_{ori}-RFU_0)$. The original protein solution and solution of NC group diluted at a corresponding ratio had the same volume, and the volume of the penetrating solution was basically the same as those of the original protein solution and the solution of NC group. It can be seen from Table 10 that, as the polymer chain length increased, the capture rate (binding efficiency, binding rate) of protein products by the nickel magnetic beads increased as well. The protein binding efficiency of L15 (2.08 mol/L sodium acrylate) $RFU_{320}$ and L18 (2.496 mol/L sodium acrylate) $RFU_{310}$ were 85% and 99%, respectively; the protein binding efficiency of L18 was increased by 16.5%.

In Table 11, by using high-concentration protein solution, the protein binding efficiency of L15 (2.08 mol/L sodium acrylate) and L18 (2.496 mol/L sodium acrylate) were 41.78% and 55.55%, respectively, and the protein binding capacity per unit volume of the magnetic beads are 40.0 μg/μL and 61.7 μg/μL, respectively. The protein binding efficiency of L18 with longer polymer chains and more branched chains and the protein binding capacity per unit volume of the magnetic beads were higher, they were increased by 33.0% and 54.5%, respectively.

In addition, the results of SDS-PAGE electrophoresis detection of the eluate containing protein products showed that compared with the purity of L15 (2.08 mol/L sodium acrylate), the purity of L18 (2.496 mol/L sodium acrylate) was also increased.

TABLE 10

Comparison of purification results of nickel magnetic beads polymerized with 2.08 mol/L and 2.496 mol/L sodium acrylate

| L15 2.08 mol/L sodium acrylate | | | | L18 2.496 mol/L sodium acrylate (having a longer chain) | | | |
|---|---|---|---|---|---|---|---|
| RFU mean | | | | RFU mean | | | |
| Original protein solution $RFU_{ori}$ | NC group $RFU_0$ | Penetrating solution $RFU_{ft}$ | Protein binding efficiency | Original protein solution $RFU_{ori}$ | NC group $RFU_0$ | Penetrating solution $RFU_{ft}$ | Protein binding efficiency |
| 21 | 3 | 4 | 94% | 32 | 1 | 2 | 96.8% |
| 38 | 3 | 4 | 97% | 58 | 2 | 3 | 98.2% |
| 79 | 5 | 8 | 96% | 127 | 5 | 7 | 98.4% |
| 153 | 7 | 21 | 90% | 310 | 6 | 8 | 99.3% |
| 320 | 14 | 61 | 85% | 556 | 7 | 11 | 99.3% |

TABLE 11

Comparison of purification results of biomagnetic beads polymerized with 2.08 mol/L and 2.496 mol/L sodium acrylate (the volume of magnetic beads is 2 μL)

| Concentration of sodium acrylate | Form of measurement | Original protein solution | Penetrating solution | Eluent 1 | Eluent 2 | Protein binding efficiency | Binding capacity (mg/mL) |
|---|---|---|---|---|---|---|---|
| L15 | RFU value | 2820 | 323 | 10891 | 1902 | / | / |
| 2.08 mol/L | Concentration (μg/mL) | 191.3 | 18.8 | 872.9 | 126.2 | / | / |
| | Volume (mL) | 1 | 1 | 0.08 | 0.08 | / | / |
| | Protein amount (μg) | 191.3 | 18.8 | 69.8 | 10.1 | 41.78% | 40.0 |
| L18 | RFU value | 4521 | 879 | 16085 | 1140 | | |
| 2.496 mol/L | Concentration (μg/mL) | 317.5 | 56.0 | 1469.8 | 73.7 | / | / |
| | Volume (mL) | 0.7 | 0.7 | 0.08 | 0.08 | / | / |
| | Protein amount (μg) | 222.3 | 39.2 | 117.6 | 5.9 | 55.55% | 61.7 |

Concentration: the concentration of the protein product is obtained by using the conversion formula in section 2.1. in Example 2.

Protein binding efficiency=(Eluent 1+Eluent 2)/Original protein solution, based on the amount of protein.

The protein binding amount per unit volume of magnetic beads=(protein amount of eluate 1+protein amount of eluate 2)/volume of magnetic beads, also known as binding capacity, in mg/mL or μg/μL.

Binding capacity: the protein binding amount per unit volume of magnetic beads.

The above description is only some of the embodiments of the invention, and the invention is not limited to the above embodiments.

All documents mentioned in the present invention are incorporated by reference in this application, just as each document is individually incorporated by reference. In addition, it should be understood that, those skilled in the art, after reading the above-taught content of the present invention, can make various changes or modifications to the present invention, and these equivalent forms also fall within the scope as defined by the appended claims of the present invention.

What is claimed is:

1. A preparation method for a magnetic microsphere, comprising following steps:

(1) performing a chemical modification on a magnetic microsphere body to form a magnetic microsphere A, wherein the chemical modification introduces an amino group onto an outer surface of the magnetic microsphere body:

(2) utilizing reaction between a carboxyl group and the amino group to covalently couple an acrylic acid molecule onto an outer surface of the magnetic microsphere A, thereby introducing a carbon-carbon double bond, and forming a magnetic microsphere B;

(3) in the absence of any cross-linking agent, utilizing polymerization reaction of carbon-carbon double bonds, polymerizing acrylic monomer molecules dissolved in a solvent to form a linear polymer, wherein the linear polymer is covalently coupled to an outer surface of the magnetic microsphere B, the linear polymer comprises a linear main chain, the linear main chain carries at least one branched chain containing a functional group; then performing a solid-liquid separation to remove liquid phase, and forming a magnetic microsphere C; and (4) coupling specific binding sites at the branched chains of the linear polymer of the magnetic microsphere C, wherein the specific binding sites are nickel ions, capable of specifically binding to a His-tagged marker.

2. The preparation method according to claim 1, wherein the step (4) comprises:

coupling a tri-carboxyl amine at each branched chain of the linear polymer of the magnetic microsphere C; subsequently, complexing a nickel ion through three carboxyl groups of tri-carboxyl amine residue to form a magnetic microsphere D, wherein the magnetic microsphere D is capable of specifically binding to a His-tagged marker.

3. The preparation method according to claim 2, wherein the tri-carboxyl amine is N, N-bis (carboxymethyl)-L-lysine.

4. The preparation method according to claim 3, wherein the amount of the N, N-bis (carboxymethyl)-L-lysine is in a range from 0.5 g/L to 550 g/L.

5. The preparation method according to claim 1, wherein the concentration of the acrylic acid molecule used for preparing the magnetic microsphere B in the step (2) is 0.002 mol/L-20 mol/L; and the acrylic monomer molecules are sodium acrylate monomer molecules; the concentration of the sodium acrylate monomer molecules used for preparing the magnetic microsphere C in the step (3) is 0.53 mol/L-12.76 mol/L.

6. The preparation method according to claim 1, wherein the magnetic microsphere body is chemically modified using a silane coupling agent.

7. A preparation method for a magnetic microsphere, comprising following steps:

(I) performing a chemical modification on a magnetic microsphere body by reacting with a trimethoxysilylated acrylic molecule to form a magnetic microsphere B, wherein the chemical modification introduces a carbon-carbon double bond onto an outer surface of the magnetic microsphere body;

(II) in the absence of any cross-linking agent, utilizing polymerization reaction of carbon-carbon double bonds, polymerizing acrylic monomer molecules dissolved in a solvent to form a linear polymer, wherein the linear polymer is covalently coupled to an outer surface of the magnetic microsphere B, the linear polymer comprises a linear main chain, the linear main chain carries at least one branched chain containing a functional group; then performing a solid-liquid separation to remove liquid phase, and forming a magnetic microsphere C; and (4) coupling specific binding sites at the branched chains of the linear polymer of the magnetic microsphere C, wherein the specific binding sites are nickel ions, capable of specifically binding to a His-tagged marker.

8. The preparation method according to claim 7, wherein the trimethoxysilylated acrylic molecule is γ-methacryloxypropyltrimethoxysilane.

9. The preparation method according to claim 7, wherein the step (4) comprises:

coupling a tri-carboxyl amine at each branched chain of the linear polymer of the magnetic microsphere C; subsequently, complexing a nickel ion through three carboxyl groups of tri-carboxyl amine residue to form a magnetic microsphere D, wherein the magnetic microsphere D is capable of specifically binding to a His-tagged marker.

10. The preparation method according to claim 9, wherein the tri-carboxyl amine is N, N-bis (carboxymethyl)-L-lysine.

11. The preparation method according to claim 10, wherein the amount of the N, N-bis (carboxymethyl)-L-lysine is in a range from 0.5 g/L to 550 g/L.

* * * * *